US006251872B1

United States Patent
Barbet et al.

(10) Patent No.: US 6,251,872 B1
(45) Date of Patent: Jun. 26, 2001

(54) **NUCLEIC ACID VACCINES FOR *EHRLICHIA CHAFFEENSIS* AND METHODS OF USE**

(75) Inventors: Anthony F. Barbet, Archer, FL (US); Roman Reddy Ganta, Manhattan, KS (US); Travis C. McGuire, Pullman, WA (US); Michael J. Burridge, Gainesville, FL (US); Aceme Nyika, Harare (ZW); Fred R. Rurangirwa, Pullman, WA (US); Suman M. Mahan, Harare (ZW); Michael V. Bowie, Gainesville; Arthur Rick Alleman, Alachua, both of FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 08/953,326

(22) Filed: Oct. 17, 1997

Related U.S. Application Data

(63) Continuation-in-part of application No. 08/733,230, filed on Oct. 17, 1996, now Pat. No. 6,025,338.

(51) Int. Cl.[7] .............................. A01N 43/04; A61K 31/70
(52) U.S. Cl. ........................ 514/44; 435/320.1; 536/23.7
(58) Field of Search .............................. 514/44; 536/23.1, 536/23.7; 435/69.3, 320.1

(56) References Cited

U.S. PATENT DOCUMENTS

| 4,879,213 | | 11/1989 | Fox et al. . |
| 5,643,578 | * | 7/1997 | Robinson et al. . |
| 5,783,441 | * | 7/1998 | Carl et al. . |

FOREIGN PATENT DOCUMENTS

| WO 90/12030 | * | 10/1990 | (WO) . |
| 9012030 | | 10/1990 | (WO) . |
| 9816554 | | 4/1998 | (WO) . |

OTHER PUBLICATIONS

Mahan et al, Microbiology 140:2135–2142, 1994.*
Reddy et al, Clin.Diag.Lab.Immun. 3:417–422, Jul. 1996.*
Oberle et al, Gene 136:291–294, 1993.*
Danko et al, Vaccine 12:1499–1553, 1994.*
Mahan et al, Microbiology, 140:2135–2142, 1994.*
Rurangirwa et al, PNAS, 96(6): 3171–3176, 1999, abstract only.*
Lewis et al, Am. J. Vet. Res, 36(1): 85–88, 1975, abstract only.*
Vemulapalli, J. Clin Microbiol, 33(11): 2987–2993, 1995, abstract only.*
Breitschwerdt et al, Antimicrobial Agents and Chemotherapy, 42(2):362–368, 1998, abstract only.*
Dutta et al, J. Clin, Miciobiol., 36(2): 506–512, 1998, abstract only.*

Bowie, Michael V. et al. (1999) "Potential Value of Major Antigenic Protein 2 for Serological Diagnosis of Heartwater and Related Ehrlichial Infections" Clinical and Diagnostic Laboratory Immunology 6(2):209–215.

Nyika, A. et al. (1999) "A DNA vaccine protects mice against the rickettsial agent *Cowdria ruminantium*" Parasite Immunology 20: 111–119.

McGuire, Travis.C., Edward B. Stephens, Guy H. Palmer, Terry F. McElwain, Carol A. Lichtensteiger, Steve R. Lieb, Anthony F. Barbet (1994) "Recombinant vaccinia virus expression of *Anaplasma marginale* surface protein MSP–1A: effect of promoters, lead sequences and GPI anchor sequence on antibody response" Vaccine 12(5):465–471.

Lazar, Eliane, Shinichi Watanable, Stephen Dalton, Michael B. Sporn (1988) "Transforming Growth Factor α: Mutation of Aspartic Acid 47 and Leucine 48 Results in Different Biological Activities" Molecular and Cellular Biology 8(3):1247–1252.

Burgess, Wilson H., Anne M. Shaheen, Mark Ravera, Michael Jaye, Patrick J. Donohue, Jeffrey A. Winkles (1990) "Possible Dissociation of the Heparin–binding and Mitogenic Activities of Heparin–binding (Acidic Fibroblast) Growth Factor–1 from Its Receptor–bdining Activities by Site–directed Mutagenesis of a Single Lysine Residue" Journal of Cell Biology 111:2129–2138.

Oberle, Suzan M., Anthony F. Barbet (1993) "Derivation of the complete msp4 gene sequence of Anaplasma marginale without cloning" Gene 136:291–294.

Reddy, G. Roman, C.R. Sulsona, R.H. Harrison, S.M. Mahan, M.J. Burridge, A.F. Barbet (1996) "Sequence Heterogeneity of the Major Antigenic Protein 1 Genes from *Cowdria ruminantium* Isolates from Different Geographical Areas" Clinical and Diagnostic Laboratory Immunology 3(4):417–422.

Lazar, Eliane, Shinichi Watanable, Stephen Dalton, Michael B. Sporn (1988) "Transforming Growth Factor α: Mutation of Aspartic Acid 47 and Leucine 48 Results in Different Biological Activities" Molecular and Cellular Biology 8(3): 1247–1252.

DuPlessis, J.L. (1970) "Immunity in Heartwater: I.A. Preliminary note On The Role of Serum Antibodies" Onderstepoort J. Vet Res. 37(3): 147–150.

Uilenberg, Gerrit (1983) "Heartwater (*Cowdria ruminantium* Infection): Current Status" Advances in Veterinary Science and Comparative Medicine 27:427–480.

(List continued on next page.)

*Primary Examiner*—Patricia A. Duffy
(74) *Attorney, Agent, or Firm*—Saliwanchik, Lloyd & Saliwanchik

(57) ABSTRACT

Described are nucleric acid vaccines containing genes to protect animals or humans against *Ehrlichia chaffeensis*. Also described are polypeptides and methods of using these polypeptides to detect antibodies to pathogens.

9 Claims, 8 Drawing Sheets

OTHER PUBLICATIONS

Vishwanath, Suryanarayanan, Gregory A. McDonald, Nancy G. Watkins (1990) "A Recombinant *Rickettsia conorii* Vaccine Protects Guinea Pigs from Experimental Boutonneuse Fever and Rocky Mountain Spotted Fever" Infection and Immunity 58(3):646–653.

van Vliet, A., F. Jongejan, M. vanKleef, B. Zeijst van der (1994) "Molecular Cloning, Sequence Analysis, and Expression of the Gene Encoding the Immunodorminant 32–Kilodalton Protein of *Cowdria ruminanthium*" Infection and Immunity 62(4):1451–1456.

Ulmer, J.B. et al. (1993) "Heterologous Protection Against Influenza by Injection of DNA Encoding a Viral Protein" Science 259:1745–1749.

Schödel, M.–T. Aguado, P.–H. Lambert (1994) "Introduction: Nucleic Acid Vaccines, WHO, Geneva, May 17–18, 1994" Vaccine 12(16):1491–1492.

Sedegah, Martha, Richard Hedstrom, Peter Hobart, Stephen L. Hoffman (1994) "Protection against malaria by immunization with plasmid DNA encoding circumsporozoite protein" Proc. Natl. Acad. Sci. USA 91:9866–9870.

Cox, J.M. Graham, Tim J. Zamb, Lorne A. Babiuk (1993) "Bovine Herpesvirus 1: Immune Responses in Mice and Cattle Injected with Plasmid DNA" Journal of Virology 67(9):5664–5667.

Burgess, Wilson H., Anne M. Shaheen, Mark Ravera, Michael Jaye, Patrick J. Donohue, Jeffrey A. Winkles (1990) "Possible Dissociation of the Heparin–binding and Mitogenic Activities of Heparin–binding (Acidic Fibroblast) Growth Factor–1 from Its Receptor–bdining Activities by Site–directed Mutagenesis of a Single Lysine Residue" Journal of Cell Biology 111:2129–2138.

Ulmer, Jeffrey B., John J. Donnelly, Margaret A. Liu (1996) "DNA Vaccines Promising: A New Approach to Inducing Protective Immunity" ASM News 62(9):476–479.

Sumner, John W., Kim G. Sims, Dana C. Jones, Burt E. Anderson (1995) "Protection of guinea–pigs from experimental Rocky Moutain spotted fever by immunization with baculovirus–expressed *Rickettsia rickettsii* rOmpA protein" Vaccine 13(1):29–35.

* cited by examiner

FIG. 1A

```
C.r.  ATGAATTGCAAGAAAAATTTTA------------TCACAAGTACACTAATATCATTAGTG
E.c.  ATGAATTACAAAAAAAAGTTTCA------------TAACAGCG-ATTGATATCATTAATA
A.m.  ATGAATTACAGAGAATTGTTTACAGGGGCCTG-TCAGCAGCC-ACAGTCTGCGCCTGCT
      ********  *       *  **          *   *  *     *  *   *  **

C.r.  TCATTTT--TACCTGGTGTGTCCTTTTCTGATGTAATACAGGAAGACAGCAACCCAGCAG
E.c.  TCCTTCTCTTACCTGGAGTATCATTTTCCGACCCAAGGCAGGTAGTGGTCA----TTAACG
A.m.  CCCTACTTGTTAGTGGGGCCGTAGTGCCATCTCCCATGAGTCACGAAGTGGCTTCTGAAG
      *  * *    * * * *  *  *     *       *    *   *  *   * *   *

C.r.  GCAGTGTTTACATTAGCGCAAAATACATGCCAACTGCATCACATTTGGTAAAATGTCAA
E.c.  GTAATTTCTACATCAGTGAGGAAAATACAACAGTTGGAGTCCAAGGCTTCGCATTTGGAGTATTCCTG
A.m.  GGGGAGTAATGGGAGGTAGCTTTTACGTGGGTGCGGCCT-ACAGCCCAGCATTTCCTTCT
       *     *  * *     *     * **  * *    *       * * *   **  *

C.r.  TCAAAGAAGATTCAAAAAATACTCAAACGGTATTGGTCTAAAAAAAGATTGGATGGCG
E.c.  CTAAGGAAGAAAGAAATACAACAGTTGGAGTGTTGGACTGAAGCAAAATTGGGACGGAA
A.m.  GTTACCTCGTTCGACATGCGTGAGTCAAGCAAAGAGACCTCA---TACGTTAGAGGCTATG
       *  *   *  *    *   *       *   *     *    *  *     *  *

C.r.  TTAAAACACCATCCAGATTCTAGCAATACTAATTCTACACAATTTTACTGAAAAAGACTATT
E.c.  GCGCAATATC--CAACTCCTCCCCAAACGA------TGTATTCACTGTCTCAATTATT
A.m.  ACAAGAGCATTGCAACGATTGAGTGTGCCAGCAAACTTTCCAAATCTGGCTACA
       *   *  *  *  *    * *  *         * *    **    *    **

C.r.  CTTTCAGATATGAAAAACAATCCGTTTTTAGGTTTTCGCTGGAGCAATTGGGTACTCAATGA
E.c.  CATTTAAATATGAAAAACAACCCGTTTTTAGGTTTTGCAGGAGCTATTGTTACTCAATGG
A.m.  CTTTTGCCTTCTCTAAAACTTAATCACGTCTCTTTCGACGGCGCTGTGTGGGATATTCTGG
       ** *    **       **        **   *  **   * ** **  *    * * **
```

FIG. 1B

```
C.r.  ATGGACCAAGAATAGAGTTCGAAGTATCCTATGAAACTTTTGATGTAAAAAACCTAGTTG
E.c.  ATGGTCCAAGAATAGAGAGCTTGAAGTATCTTATGAAACATTTGATGTAAAAAATCAAGTA
A.m.  GAGGAGCCAGAGTGGAATTGGAAGCGAGCTACAGAAGGTTTGCTACTTTGGCGGACGGGC
       **   ****   ***   *   **    *  **  *  *****   *

C.r.  GCAACTATAAAAACAACGCACACATGTACTGTGCTTTAGATACAGCAGCACAAAATAGCA
E.c.  ACAATTATAAGAATGAAGCACACATAGATATTGTGCTCTATCCCATACTCAGCAGCAGACA
A.m.  AGTACGCAAAAAGTG---------GTGCGGAATCTCTGGCAGCTATTACCCGCG
       *  *                    ****      *          *  *  *

C.r.  CTAATGGCGCAGGATTAACTACATCTGTTATGGTAAAAACGAAAATTTAACAAATATAT
E.c.  TGAGTAGTGCAAG---TAATAATTTTGTCTTTCTAAAAAATGAAGGATTACTTGACATAT
A.m.  ACGCTAACATTACTGAGACCAATTACTTCGTAGTACAGATTGATGAAATCACAAACACCT
           *    **   *   **      **  **     **  **       *   *

C.r.  CATTAATGTTAAATGCGTGTTATGATATCATGCTTGATGGAATACCAGTTTCTCCATATG
E.c.  CATTTATGCTGAACGCATGCTATGACGTAGTAGGCTAGTAGGCCATACCTTTTTCTCCTTATA
A.m.  CAGTCATGTTAAATGGCTGCTATGACGTGCTGCACACAGATTACCTGTGCCCGTATG
       *  *  ***  **   **  **     *  *       **   **        **

C.r.  TATGTGCAGGTATTGGCACTGACTTAGTGTCAGTAATTAATGCTACAAATCCTAAATTAT
E.c.  TATGCTCCAGGTATCGGTACTGATTAGTATCCATGTTTGAAGCTACAAATCCTAAAATTT
A.m.  TATGTGCCGGGATAGGCGCAAGCTTTGTTGACATCTCTAAGCAAGTAACCACAAAGCTGG
       ****    **  **   **        *      **       **  **    **  ***

C.r.  CTTATCAAGGAAAGCTAGGCATAAGTTACTCAATCAATTCTGAAGCTTCTATCTTTATCG
E.c.  CTTACCAAGGAAAGTTAGGTTTAAGCTACTCCTATAAGCCCCAGAAGCTTCTGTGTTATTG
A.m.  CCTACAGGGGCAAGTTGGGATTAGCTACCAGTTTACTCCAGTTTACTCCGGAAATATCCTTGGTGCCAG
       *   **  **    *    **   ***    **       *          **   *

```
C.r.  GTGGACATTCCCATAGAGTTATAGGTAATTAAAGATATTGCTACCTTAAAAATAT
E.c.  GTGGGCACTTTCATAGGTAATAGGGAATTTAGAGATATTCCTACTATAATACCTA
A.m.  GTGGGTTCTACCACGGGCTATTTGATGAGTCTTACAAGGACATTCCCGCACACAACAGTG
      ****  *   *  *       *         *  **  ****  *   **  **

C.r.  TTACTTCAAAACAGGAATATCTAATCCTGCCTTTGCATCAGCAACACTTGATGTTTGTC
E.c.  CTGGATCAACACTTGCAGGAAAAGGAAACTACCCTGCAATAGTAATACTGGATGTATGCC
A.m.  TAAAGTTCTCTGGAGAAGCAAAA------------GCCTCAGTCAAAGCGCATATTGCTG
         *     *  *     **         **     *   **   *   **   *

C.r.  ACTTTGGTATAGAAATTGGAGGAAGGTTTGTATTTTAA---
E.c.  ACTTTGGAATAGAAATGGGAGGAGGAAGGTTTAA-------
A.m.  ACTACGGCTTTAACCTTGGAGCAAGATTCCTGTTCAGCTAA
      ***  *  *   *  * *  * *  *     **
```

```
  1 ggaatgaattcagggacatttctactcttaaagcgtttgctacaccatcatctgcagcta
     N  E  F  R  D  I  S  T  L  K  A  F  A  T  P  S  S  A  A  T
 61 ctccagacttagcaacagtaacactgagtgtgtgtcactttggagtagaacttggaggaa
     P  D  L  A  T  V  T  L  S  V  C  H  F  G  V  E  L  G  G  R
121 gatttaacttctaattttattattgccacatgttaaaaataatctaaacttgttttcatt
     F  N  F  *
181 attgctacaaataaataaaatagtggcaaaaaaatgtagcaataagagggggggggggga
241 ctaattactatctgccatatcccttactaccacttacactaaataatctgacaaatacaa
301 cagcttctggagaaataaacaatatttaattttttcttacaaaaaccatttatatcttgt
                                                     -35
361 actaaaaactagcttataacttgttttttacattgtaggtttactactgttaatttgtttt
                    -10
421 cactatttaggtgtaatatgaactgcgaaaaattttttataacaactgcattaacatta
              RBS     M  N  C  E  K  F  F  I  T  T  A  L  T  L
481 ctaatgtccttcttacctggaatatcactttctgatccagtacaggatgacaacattagt
     L  M  S  F  L  P  G  I  S  L  S  D  P  V  Q  D  D  N  I  S
541 ggtaatttctacatcagtggaaagtatatgccaagcgcttcgcatttggagtttttct
     G  N  F  Y  I  S  G  K  Y  M  P  S  A  S  H  F  G  V  F  S
601 gccaaggaagaaagaaatacaacagttggagtatttggaatagagcaagattgggataga
     A  K  E  E  R  N  T  T  V  G  V  F  G  I  E  Q  D  W  D  R
661 tgtgtaatatctagaaccactttaagcgatatattcaccgttccaaattattcatttaag
     C  V  I  S  R  T  T  L  S  D  I  F  T  V  P  N  Y  S  F  K
721 tatgaaaataatctattttcaggatttgcaggagctattggctactcaatggatggccca
     Y  E  N  N  L  F  S  G  F  A  G  A  I  G  Y  S  M  D  G  P
781 agaatagagcttgaagtatctTatgaagcattcgatgttaaaaatcaaggtaacaattat
     R  I  E  L  E  V  S  Y  E  A  F  D  V  K  N  Q  G  N  N  Y
841 aagaacgaagcacatagatattatgctctgtcccatcttctggcacagagacagata
     K  N  E  A  H  R  Y  Y  A  L  S  H  L  L  G  T  E  T  Q  I
901 gatggtgcaggcagtgcgtctgtctttctaataaatgaaggactacttgataaatcattt
     D  G  A  G  S  A  S  V  F  L  I  N  E  G  L  L  D  K  S  F
961 atgctgaacgcatgttatgatgtaataagtgaaggcatacctttttctccttatatatgt
     M  L  N  A  C  Y  D  V  I  S  E  G  I  P  F  S  P  Y  I  C
1021 gcaggtattggtattgatttagtatccatgtttgaagctataaatcctaaaatttcttat
      A  G  I  G  I  D  L  V  S  M  F  E  A  I  N  P  K  I  S  Y
1081 caaggaaaattaggcttaagttaccctataagcccagaagcttctgtgtttattggtgga
      Q  G  K  L  G  L  S  Y  P  I  S  P  E  A  S  V  F  I  G  G
1141 catttcataaggtgataggaaacgaatttagagatattcctactatgatacctagtgaa
      H  F  H  K  V  I  G  N  E  F  R  D  I  P  T  M  I  P  S  E
1201 tcagcgcttgcaggaaaaggaaactaccctgcaatagtaacactggacgtgttctacttt
      S  A  L  A  G  K  G  N  Y  P  A  I  V  T  L  D  V  F  Y  F
1261 ggcatagaacttggaggaaggtttaacttccaactttgattattgccacaataaataaaa
      G  I  E  L  G  G  R  F  N  F  Q  L  *
1321 atagtggcaaaagaatgtagcaataagagggggggaggggggaactaaattattatttgcc
1381 atatcccttactaccacttacaccaaataatctgacaaatacaacagttcaaacaaaggt
1441 aaacaattcttaaatttgtcttatgagaaccattgatatcttatattaaaaactagctta
                                           -35
1501 taacttgtctttacattgcagttctactattgttaatttattttcactattttaggtgta
     -10                                                     RBS
1561 atatgaattgcaaaaaatttttttataacaactgcattagtatcactaatgtcctttctac
        M  N  C  K  K  F  F  I  T  T  A  L  V  S  L  M  S  F  L  P
1621 ctggaatatcattttctgatccagtgcaaggtgacaatattagtggtaatttctatgtta
      G  I  S  F  S  D  P  V  Q  G  D  N  I  S  G  N  F  Y  V  S
1681 gtggcaagtatatgccaagtgcttcgcatttggcatgtttttctgccaaagaagaaaaaa
      G  K  Y  M  P  S  A  S  H  F  G  M  F  S  A  K  E  E  K  N
1741 atcctactgttgcattgtatggcttaaaacaagattgggaagggattagctcatcaagtc
      P  T  V  A  L  Y  G  L  K  Q  D  W  E  G  I  S  S  S  H
1801 acaatgataatcatttcaataacaagggttattcatttaaatatgaaaataacccattt
      N  D  N  H  F  N  N  K  G  Y  S  F  K  Y  E  N  N  P  F  L
1861 tagggtttgcaggagctattggttattcaatgggtggtccaagagtagagtttgaagtgt
      G  F  A  G  A  I  G  Y  S  M  G  G  P  R  V  E  F  E  V  S
1921 cctatgaaacatttgacgttaaaaatcagggtaataactataaaaatgatgctcacagat
      Y  E  T  F  D  V  K  N  Q  G  N  N  Y  K  N  D  A  H  R  Y
1981 actgtgctttaggtcaacaagacaacagcggaatacctaaaactagtaaatacgtactgt
      C  A  L  G  Q  Q  D  N  S  G  I  P  K  T  S  K  Y  V  L  L
2041 taaaaagcgaaggattgcttgacatatcatttatgctaaatgcatgctatgatataataa
      K  S  E  G  L  L  D  I  S  F  M  L  N  A  C  Y  D  I  I  N
2101 acgagagcataccttttgtctccttacatatgtgcaggtgttggtActgattttaatatcca
      E  S  I  P  L  S  P  Y  I  C  A  G  V  G  T  D  L  I  S  M
2161 tgtttgaagctacaaatcctaaaatttcttaccaagggaagttaggtctaagttactcta
      F  E  A  T  N  P  K  I  S  Y  Q  G  K  L  G  L  S  Y  S  I
2221 taaacccagaagcttctgtatttattggtggacattttcataaggtgataggaaacgaat
      N  P  E  A  S  V  F  I  G  G  H  F  H  K  V  I  G  N  E  F
2281 ttagggacattcctactctgaaagcatttgttacgtcatcagctactccagatctagcaa
      R  D  I  P  T  L  K  A  F  V  T  S  S  A  T  P  D  L  A  I
```

FIG. 2A

```
2341 tagtaacactaagtgtatgtcattttggaatagaacttggaggaaggtttaacttctaat
      V  T  L  S  V  C  H  F  G  I  E  L  G  G  R  F  N  F  *
2401 tttgttattgccacatgttaaaaataatctaaacttgttttcattattgctacagtaaat
2461 aaaaatagtggcaaaagaatgtagcaataagaagggggggggggggactaaattgctattt
2521 accatatcccttattataccacttacactaaataacttgacaaatacaacagcttctgga
2581 aaaacaaacaatacttaaatttctcttacaaaaaccatttatatcttgtactaaaaacta
                                            -35
2641 gcttataacttgttttttacattgtagttctactattgttaatttattttcactattttag
        -10
2701 gtgcaatatgaattgcaaaaaattttttataacaactacattagtatcgctaatgtcctt
     RBS   M  N  C  K  K  F  F  I  T  T  T  L  V  S  L  M  S  F
2761 cttacctggaatatcattttctgatgcagtacagaacgacaatgttggtggtaatttcta
      L  P  G  I  S  F  S  D  A  V  Q  N  D  N  V  G  G  N  F  Y
2821 tatcagtgggaaatatgtaccaagtgttttcacattttggcgtattctctgctaaacagga
      I  S  G  K  Y  V  P  S  V  S  H  F  G  V  F  S  A  K  Q  E
2881 aagaaatacaacaatcggagtatttggattaaagcaagattgggatggcagcacaatatc
      R  N  T  T  I  G  V  F  G  L  K  Q  D  W  D  G  S  T  I  S
2941 taaaaattctccagaaaatacatttaacgttccaaa_ttattcatttaaatatgaa_aataa
      K  N  S  P  E  N  T  F  N  V  P  N  Y  S  F  K  Y  E  N  N
3001 tccatttctaggttttgcaggagctgttggttatttaatgaatggtccaagaatagagtt
      P  F  L  G  F  A  G  A  V  G  Y  L  M  N  G  P  R  I  E  L
3061 agaaatgtcctatgaaacatttgatgtgaaaaaccagggtaataactataagaacgatgc
      E  M  S  Y  E  T  F  D  V  K  N  Q  G  N  N  Y  K  N  D  A
3121 tcacaaatattatgctttaacccataacagtgggggaaagctaagcaatgcaggtgataa
      H  K  Y  Y  A  L  T  H  N  S  G  G  K  L  S  N  A  G  D  K
3181 gtttgtttttctaaaaaatgaaggactacttgatatatcacttatgttgaatgcatgcta
      F  V  F  L  K  N  E  G  L  L  D  I  S  L  M  L  N  A  C  Y
3241 tgatgtaataagtgaaggaatacctttctctccttacatatgcaggtgttggtactga
      D  V  I  S  E  G  I  P  F  S  P  Y  I  C  A  G  V  G  T  D
3301 tttaatatccat_gtttgaagctataaacc_ctaaaatttcttatcaaggaaagttaggttt
      L  I  S  M  F  E  A  I  N  P  K  I  S  Y  Q  G  K  L  G  L
3361 gagttactccataagcccagaagcttctgttttgttggtggacatttcataaggtgat
      S  Y  S  I  S  P  E  A  S  V  F  V  G  H  F  H  K  V  I
3421 agggaatgaattcagagatattcctgctatgataccagtacctcaactctcacaggtaa
      G  N  E  F  R  D  I  P  A  M  I  P  S  T  S  T  L  T  G  N
3481 tcactttactatagtaacactaagtgtatgccactttggagtggaacttggaggaaggtt
      H  F  T  I  V  T  L  S  V  C  H  F  G  V  E  L  G  G  R  F
3541 taacttttaatttattattgccacatgttaaaaataatctaaacttgttttttattattg
      N  F  *
3601 ctgcaggtaaataaaaatagtggcaaaagaatgtagcaataagagggggggggggactag
3661 tttataagtgctgttttctcacctttacacatgatactatacttaaccagttttttttgc
3721 tattacttacctgacgtaatatattaaattttccttacaaaagttaccgatattttatac
                                                       -35
3781 aaaaatttatattctgacttgcttttatatgacacttctactattgttaatttatttgtc
           -10
3841 actattaggttatatatgaattacaaaaaagttttcataacaagtgcattgatatcatta
            RBS   M  N  Y  K  K  V  F  I  T  S  A  L  I  S  L
3901 atatcttctctacctggagtatcattttccgacccagcaggtagtggtattaacggtaat
      I  S  S  L  P  G  V  S  F  S  D  P  A  G  S  G  I  N  G  N
3961 ttctacatcagtggaaaatacatgccaagtgcttcgcatttggagtattctctgctaag
      F  Y  I  S  G  K  Y  M  P  S  A  S  H  F  G  V  F  S  A  K
4021 gaagaaagaaatacaacagttggagtgtttggactgaagcaaaattgggacggaagcgca
      E  E  R  N  T  T  V  G  V  F  G  L  K  Q  N  W  D  G  S  A
4081 atatccaactcctcccaaacgatgtattcactgtctcaaa_ttattcatttaaatatgaa_
      I  S  N  S  S  P  N  D  V  F  T  V  S  N  Y  S  F  K  Y  E
4141 aacaacccgttttttaggttttgcaggagctattggttactcaatggatggtccaagaata
      N  N  P  F  L  G  F  A  G  A  I  G  Y  S  M  D  G  P  R  I
4201 gagcttgaagtatcttatgaaacatttgatgtaaaaaatcaaggtaacaattataagaat
      E  L  E  V  S  Y  E  T  F  D  V  K  N  Q  G  N  N  Y  K  N
4261 gaagcacatagatattgtgctctatcccataactcagcagcagacatgagtagtgcaagt
      E  A  H  R  Y  C  A  L  S  H  N  S  A  A  D  M  S  S  A  S
4321 aataattttgtctttctaaaaaatgaaggattacttgacatatcatttatgctgaacgca
      N  N  F  V  F  L  K  N  E  G  L  L  D  I  S  F  M  L  N  A
4381 tgctatgacgtagtaggcgaaggcatacctttttctccttatatatgcgcaggtatcggt
      C  Y  D  V  V  G  E  G  I  P  F  S  P  Y  I  C  A  G  I  G
4441 actgatttagtatccat_gtttgaagctacaaatcc_taaaatttcttaccaaggaaagtta
      T  D  L  V  S  M  F  E  A  T  N  P  K  I  S  Y  Q  G  K  L
4501 ggtttaagctactctataagcccagaagcttctgtgtttattggtgggcactttcataag
      G  L  S  Y  S  I  S  P  E  A  S  V  F  I  G  G  H  F  H  K
4561 gtaatagggaacgaatttagagatattcctactataatacctactggatcaacacttgca
      V  I  G  N  E  F  R  D  I  P  T  I  I  P  T  G  S  T  L  A
4621 ggaaaaggaaactaccctgcaataataactggatgtatgccactttggaatagaaatg
      G  K  G  N  Y  P  A  I  V  I  L  D  V  C  H  F  G  I  E  M
4681 gga
      G
```

FIG. 2B

```
   1 tggtgtaaatatgaaatataaaaaacttttacagtaactgcattagtattattaacttc
     RBS      M  K  Y  K  K  T  F  T  V  T  A  L  V  L  L  T  S
  61 ctttacacattttatacctttttatagtccagcacgtgccagtacaattcacaacttcta
      F  T  H  F  I  P  F  Y  S  P  A  R  A  S  T  I  H  N  F  Y
 121 cattagtggaaaatatatgccaacagcgtcacattttggattttttcagctaagaaga
      I  S  G  K  Y  M  P  T  A  S  H  F  G  I  F  S  A  K  E  E
 181 acaaagttttactaaggtattagttgggttagatcaacgattatcacataatattataaa
      Q  S  F  T  K  V  L  V  G  L  D  Q  R  L  S  H  N  I  I  N
 241 caataatgatacagcaaagagtcttaaggttcaaaattattcatttaaatacaaaaataa
      N  N  D  T  A  K  S  L  K  V  Q  N  Y  S  F  K  Y  K  N  N
 301 cccatttctaggatttgcaggagctattggttattcaataggcaattcaagaatagaact
      P  F  L  G  F  A  G  A  I  G  Y  S  I  G  N  S  R  I  E  L
 361 agaagtatcacatgaaatatttgatactaaaaacccaggaaacaattatttaaatgactc
      E  V  S  H  E  I  F  D  T  K  N  P  G  N  N  Y  L  N  D  S
 421 tcacaaatattgcgctttatctcatggaagtcacatatgcagtgatggaaatagcggaga
      H  K  Y  C  A  L  S  H  G  S  H  I  C  S  D  G  N  S  G  D
 481 ttggtacactgcaaaaactgataagtttgtacttctgaaaaatgaaggtttacttgacgt
      W  Y  T  A  K  T  D  K  F  V  L  L  K  N  E  G  L  L  D  V
 541 ctcatttatgttaaacgcatgttatgacataacaactgaaaaaatgccttttcaccctta
      S  F  M  L  N  A  C  Y  D  I  T  T  E  K  M  P  F  S  P  Y
 601 tatatgtgcaggtattggtactgatctcatatctatgtttgagacaacacaaaacaaaat
      I  C  A  G  I  G  T  D  L  I  S  M  F  E  T  T  Q  N  K  I
 661 atcttatcaaggaaagttaggtttaaactatactataaactcaagagtttctgttttgc
      S  Y  Q  G  K  L  G  L  N  Y  T  I  N  S  R  V  S  V  F  A
 721 aggtgggcactttcataaggtaataggtaatgaatttaaaggtattcctactctattacc
      G  G  H  F  H  K  V  I  G  N  E  F  K  G  I  P  T  L  L  P
 781 tgatggatcaaacattaaagtacaacagtctgcaacagtaacattagatgtgtgccattt
      D  G  S  N  I  K  V  Q  Q  S  A  T  V  T  L  D  V  C  H  F
 841 cgggttagagattggaagtagattttcttttaatacttctattgtacatgttaaaaata
      G  L  E  I  G  S  R  F  F  *
 901 gtactagtttgcttctgtggtttataaacgcaagagagaaatagttagtaataaattaga
 961 aagttaaatattagaaaagtcatatgttttcattgtcattgatactcaactaaaagtag
1021 tataaatgttacttattaataattttacgtagtatattaaatttcccttacaaaagccac
1081 tagtatttttatactaaaagctatactttggcttgtatttaatttgtattttactactgt
      -35                        -10
1141 taatttactttcactgtttctggtgtaaatatgaattgtaaaaagttttcacaataagt
                             RBS      M  N  C  K  K  V  F  T  I  S
1201 gcattgatatcatccatatacttcctacctaatgtctcatactctaacccagtatatggt
      A  L  I  S  S  I  Y  F  L  P  N  V  S  Y  S  N  P  V  Y  G
1261 aacagtatgtatggtaattttacatatcaggaaagtacatgccaagtgttcctcattttt
      N  S  M  Y  G  N  F  Y  I  S  G  K  Y  M  P  S  V  P  H  F
1321 ggaattttttcagctgaagaagagaaaaaaagacaactgtagtatatggcttaaaagaa
      G  I  F  S  A  E  E  E  K  K  K  T  T  V  V  Y  G  L  K  E
1381 aactgggcaggagatgcaatatctagtcaaagtccagatgataatttaccattcgaaat
      N  W  A  G  D  A  I  S  S  Q  S  P  D  D  N  F  T  I  R  N
1441 tactcattcaagtatgcaagcaacaagttttagggtttgcagtagctattggttactcg
      Y  S  F  K  Y  A  S  N  K  F  L  G  F  A  V  A  I  G  Y  S
1501 ataggcagtccaagaatagaagttgagatgtcttatgaagcatttgatgtaaaaaatcaa
      I  G  S  P  R  I  E  V  E  M  S  Y  E  A  F  D  V  K  N  Q
1561 ggtaacaatt
      G  N  N
```

FIG. 2C

```
   1  acatgtatacattatagtaacaaatgttaccgtatttattcataagttaagtaaaatct 61  ataccattctctttcactttatcagaagactttatttatcacaaactcatgacgtatag 121  tgtcacaaataaacacactgcaactgcaatcactacgtaaaactttaactcttcttttc 181  acaactaaaatactaataaaagtaatatagtataaaaaatcttaagtaacTTGACAtaat
                                                       -35
 241  attactctgataTAGCATatgtctagtatctctatactaaacgtttatataattGGAGca
                 -10
 301  tattaATGAAAGCTATCAAATTCATACTTAATGTCTGCTTACTATTTGCAGCAATATTTT
            M  K  A  I  K  F  I  L  N  V  C  L  L  F  A→ A  I  F  L 361  TAGGGTATTCCTATATTACAAAACAAGGCATATTTCAAACAAAACATCATGATACACCTA
        G  Y  S  Y  I  T  K  Q  G  I  F  Q  T  K  H  H  D  T  P  N 421  ATACTACTATACCAAATGAAGACGGTATTCAATCTAGCTTTAGCTTAATCAATCAAGACG
        T  T  I  P  N  E  D  G  I  Q  S  S  F  S  L  I  N  Q  D 481  GTAAAACAGTAACCAGCCAAGATTTCCTAGGGAAACACATGTTAGTTTTGTTTGGATTCT
        K  T  V  T  S  Q  D  F  L  G  K  H  M  L  V  L  F  G  F  S 541  CTGCATGTAAAAGCATTTGCCCTGCAGAATTGGGATTAGTATCTGAAGCACTTGCACAAC
        A  C  K  S  I  C  P  A  E  L  G  L  V  S  E  A  L  A  Q  L 601  TTGGTAATAATGCAGACAAATTACAAGTAATTTTTATTACAATTGATCCAAAAAATGATA
        G  N  N  A  D  K  L  Q  V  I  F  I  T  I  D  P  K  N  D  T 661  CTGTAGAAAAATTAAAAGAATTTCATGAACATTTTGATTCAAGAATTCAAATGTTAACAG
        V  E  K  L  K  E  F  H  E  H  F  D  S  R  I  Q  M  L  T  G 721  GAAATACTGAAGACATTAATCAAATAATTAAAAATTATAAAATATATGTTGGACAAGCAG
        N  T  E  D  I  N  Q  I  I  K  N  Y  K  I  Y  V  G  Q  A  D 781  ATAAAGATCATCAAATTAACCATTCTGCAATAATGTACCTTATTGACAAAAAAGGATCAT
        K  D  H  Q  I  N  H  S  A  I  M  Y  L  I  D  K  K  G  S  Y 841  ATCTTTCACACTTCATTCCAGATTTAAAATCACAAGAAAATCAAGTAGATAAGTTACTAT
        L  S  H  F  I  P  D  L  K  S  Q  E  N  Q  V  D  K  L  L  S 901  CTTTAGTTAAGCAGTATCTGTAAtttaataattaattAAAGagaatagtacacaCTTTtt
        L  V  K  Q  Y  L  *

961  ataaattcatggaatacgttggatgagtaggttttttttagtattttagtgctaataac
1021  attggcat
```

FIG. 3A

```
  1    ggaaatctcatgtaaacgtgaaatactatattcttttttaaataccaatacaattgaata
 61    caaaaaacttttacaacttattatgtttatcttaaaaccttattttaagattccttatg
121    tcacaaaataacaaaaatactatttacaaaatacaccacaatttcatcaaataaaaaaa
181    ctatacactttattatactacagtagatataccataaaagattttaagtaacTTGACAta
                                                           -35
241    atattaccttggtaTAGCATatgattcagtattttatattaaaatttattatgtattGGA
                     -10
301    GcataaaATGAAAGTTATCAAATTTATACTTAATATCTGTTTATTATTTGCAGCAATTTT
               M  K  V  I  K  F  I  L  N  I  C  L  L  F  A →A  I  F
361    TCTAGGATATTCCTACGTAACAAAACAAGGCATTTTTCAAGTAAGAGATCATAACACTCC
        L  G  Y  S  Y  V  T  K  Q  G  I  F  Q  V  R  D  H  N  T  P
421    CAATACAAATATATCAAATAAAGCCAGCATTACTACTAGTTTTTCGTTAGTAAATCAAGA
         N  T  N  I  S  N  K  A  S  I  T  T  S  F  S  L  V  N  Q  D
481    TGGAAATACAGTAAATAGTCAAGATTTTTTGGGAAAATACATGCTAGTTTTATTTGGATT
         G  N  T  V  N  S  Q  D  F  L  G  K  Y  M  L  V  L  F  G  F
541    TTCTTCATGTAAAAGCATCTGCCCTGCTGAATTAGGAATAGCATCTGAAGTTCTCTCACA
         S  S  C  K  S  I  C  P  A  E  L  G  I  A  S  E  V  L  S  Q
601    GCTTGGTAATGACACAGACAAGTTACAAGTAATTTTCATTACAATTGATCCAACAAATGA
         L  G  N  D  T  D  K  L  Q  V  I  F  I  T  I  D  P  T  N  D
661    TACTGTACAAAAATTAAAAACATTTCATGAACATTTTGATCCTAGAATTCAAATGCTAAC
         T  V  Q  K  L  K  T  F  H  E  H  F  D  P  R  I  Q  M  L  T
721    AGGCAGTGCAGAAGATATTGAAAAAATAATAAAAAATTACAAAATATATGTTGGACAAGC
         G  S  A  E  D  I  E  K  I  I  K  N  Y  K  I  Y  V  G  Q  A
781    AGATAAAGATAATCAAATTGATCACTCTGCCATAATGTACATTATCGATAAAAAAGGAGA
         D  K  D  N  Q  I  D  H  S  A  I  M  Y  I  I  D  K  K  G  E
841    ATACATTTCACACTTTTCTCCAGATTTAAAATCAACAGAAAATCAAGTAGATAAGTTACT
         Y  I  S  H  F  S  P  D  L  K  S  T  E  N  Q  V  D  K  L  L
901    ATCTATAATAAAACAATATCTCTAAtttaataattaattaAAGAGaatagtacacaCTCT
         S  I  I  K  Q  Y  L  *
961    Tatataaattcatggatatatgtgatgggtagatttcttttggtgtttctatcgctaatt
1021   acatta
```

FIG. 3B

NUCLEIC ACID VACCINES FOR *EHRLICHIA CHAFFEENSIS* AND METHODS OF USE

CROSS-REFERENCE TO A RELATED APPLICATION

This is a continuation-in-part of U.S. patent application Ser. No. 08/733,230, filed Oct. 17, 1996 now U.S. Pat. No. 6,025,338.

This invention was made with government support under USAID Grant No. LAG-1328-G-00-3030-00. The government has certain rights in this invention.

TECHNICAL FIELD

This invention relates to nucleic acid vaccines for rickettsial diseases of animals, including humans.

BACKGROUND OF THE INVENTION

The rickettsias are a group of small bacteria commonly transmitted by arthropod vectors to man and animals, in which they may cause serious disease. The pathogens causing human rickettsial diseases include the agent of epidemic typhus, *Rickettsia prowazekii,* which has resulted in the deaths of millions of people during wartime and natural disasters. The causative agents of spotted fever, e.g., *Rickettsia rickettsii* and *Rickettsia conorii,* are also included within this group. Recently, new types of human rickettsial disease caused by members of the tribe Ehrlichiae have been described. Ehrlichiae infect leukocytes and endothelial cells of many different mammalian species, some of them causing serious human and veterinary diseases. Over 400 cases of human ehrlichiosis, including some fatalities, caused by *Ehrlichia chaffeensis* have now been reported. Clinical signs of human ehrlichiosis are similar to those of Rocky Mountain spotted fever, including fever, nausea, vomiting, headache, and rash.

Heartwater is another infectious disease caused by a rickettsial pathogen, namely *Cowdria ruminantium,* and is transmitted by ticks of the genus Amblyomma. The disease occurs throughout most of Africa and has an estimated endemic area of about 5 million square miles. In endemic areas, heartwater is a latent infection in indigenous breeds of cattle that have been subjected to centuries of natural selection. The problems occur where the disease contacts susceptible or naive cattle and other ruminants. Heartwater has been confirmed to be on the island of Guadeloupe in the Caribbean and is spreading through the Caribbean Islands. The tick vectors responsible for spreading this disease are already present on the American mainland and threaten the livestock industry in North and South America In acute cases of heartwater, animals exhibit a sudden rise in temperature, signs of anorexia, cessation of rumination, and nervous symptoms including staggering, muscle twitching, and convulsions. Death usually occurs during these convulsions. Peracute cases of the disease occur where the animal collapses and dies in convulsions having shown no preliminary symptoms. Mortality is high in susceptible animals. Angora sheep infected with the disease have a 90% mortality rate while susceptible cattle strains have up to a 60% mortality rate.

If detected early, tetracycline or chloramphenicol treatment are effective against rickettsial infections, but symptoms are similar to numerous other infections and there are no satisfactory diagnostic tests (Helmick, C., K. Bernard, L. D'Angelo [1984] *J. Infect. Dis.* 150:480).

Animals which have recovered from heartwater are resistant to further homologous, and in some cases heterologous, strain challenge. It has similarly been found that persons recovering from a rickettsial infection may develop a solid and lasting immunity. Individuals recovered from natural infections are often immune to multiple isolates and even species. For example, guinea pigs immunized with a recombinant *R. conorii* protein were partially protected even against *R. rickettsii* (Vishwanath, S., G. McDonald, N. Watkins [1990] *Infect. Immun.* 58:646). It is known that there is structural variation in rickettsial antigens between different geographical isolates. Thus, a functional recombinant vaccine against multiple isolates would need to contain multiple epitopes, e.g. protective T and B cell epitopes, shared between isolates. It is believed that serum antibodies do not play a significant role in the mechanism of immunity against rickettsia (Uilenberg, G. [1983] *Advances in Vet. Sci. and Comp. Med* 27:427–480; Du Plessis, Plessis, J. L. [1970] *Onderstepoort J. Vet. Res.* 37(3):147–150).

Vaccines based on inactivated or attenuated rickettsiae have been developed against certain rickettsial diseases, for example against *R. prowazekii* and *R. rickettsii.* However, these vaccines have major problems or disadvantages, including undesirable toxic reactions, difficulty in standardization, and expense (Woodward, T. [1981] "Rickettsial diseases: certain unsettled problems in their historical perspective," In *Rickettsia and Rickettsial Diseases*, W. Burgdorfer and R. Anacker, eds., Academic Press, New York, pp. 17–40).

A vaccine currently used in the control of heartwater is composed of live infected sheep blood. This vaccine also has several disadvantages. First, expertise is required for the intravenous inoculation techniques required to administer this vaccine. Second, vaccinated animals may experience shock and so require daily monitoring for a period after vaccination. There is a possibility of death due to shock throughout this monitoring period, and the drugs needed to treat any shock induced by vaccination are costly. Third, blood-borne parasites may be present in the blood vaccine and be transmitted to the vaccinates. Finally, the blood vaccine requires a cold chain to preserve the vaccine.

Clearly, a safer, more effective vaccine that is easily administered would be particularly advantageous. For these reasons, and with the advent of new methods in biotechnology, investigators have concentrated recently on the development of new types of vaccines, including recombinant vaccines. However, recombinant vaccine antigens must be carefully selected and presented to the immune system such that shared epitopes are recognized. These factors have contributed to the search for effective vaccines.

A protective vaccine against rickettsiae that elicits a complete immune response can be advantageous. A few antigens which potentially can be useful as vaccines have now been identified and sequenced for various pathogenic rickettsia. The genes encoding the antigens and that can be employed to recombinantly produce those antigen have also been identified and sequenced. Certain protective antigens identified for *R. rickettsii, R. conorii,* and *R. prowazekii* (e.g., rOmpA and rOmpB) are large (>100kDa), dependent on retention of native conformation for protective efficacy, but are often degraded when produced in recombinant systems. This presents technical and quality-control problems if purified recombinant proteins are to be included in a vaccine. The mode of presentation of a recombinant antigen to the immune system can also be an important factor in the immune response.

Nucleic acid vaccination has been shown to induce protective immune responses in non-viral systems and in diverse animal species (Special Conference Issue, WHO meeting on nucleic acid vaccines [1994] *Vaccine* 12:1491). Nucleic acid vaccination has induced cytotoxic lymphocyte (CTL), T-helper 1, and antibody responses, and has been shown to be protective against disease (Ulmer, J., J. Donelly, S. Parker et al. [1993] *Science* 259:1745). For example, direct intramuscular injection of mice with DNA encoding the influenza nucleoprotein caused the production of high titer antibodies, nucleoprotein-specific CTLs, and protection against viral challenge. Immunization of mice with plasmid DNA encoding the Plasmodium yoelii circumsporozoite protein induced high antibody titers against malaria sporozoites and CTLs, and protection against challenge infection (Sedegah, M., R. Hedstrom, P. Hobart, S. Hoffman [1994] *Proc. Natl. Acad. Sci. USA* 91:9866). Cattle immunized with plasmids encoding bovine herpesvirus 1 (BHV-1) glycoprotein IV developed neutralizing antibody and were partially protected (Cox, G., T. Zamb, L. Babiuk [1993] *J. Virol.* 67:5664). However, it has been a question in the field of immunization whether the recently discovered technology of nucleic acid vaccines can provide improved protection against an antigenic drift variant. Moreover, it has not heretofore been recognized or suggested that nucleic acid vaccines may be successful to protect against rickettsial disease or that a major surface protein conserved in rickettsia was protective against disease.

BRIEF SUMMARY OF THE INVENTION

Disclosed and claimed here are novel vaccines for conferring immunity to rickettsia infection, including Cowdria ruminantium causing heartwater. Also disclosed are novel nucleic acid compositions and methods of using those compositions, including to confer immunity in a susceptible host. Also disclosed are novel materials and methods for diagnosing infections by Ehrlichia in humans or animals.

One aspect of the subject invention concerns a nucleic acid, e.g., DNA or mRNA, vaccine containing the major antigenic protein 1 gene (MAP1) or the major antigenic protein 2 gene (MAP2) of rickettsial pathogens. In one embodiment, the nucleic acid vaccines can be driven by the human cytomegalovirus (HCMV) enhancer-promoter. In studies immunizing mice by intramuscular injection of a DNA vaccine composition according to the subject invention, immunized mice seroconverted and reacted with MAP1 in antigen blots. Splenocytes from immunized mice, but not from control mice immunized with vector only, proliferated in response to recombinant MAP1 and rickettsial antigens in in vitro lymphocyte proliferation tests. In experiments testing different DNA vaccine dose regimens, increased survival rates as compared to controls were observed on challenge with rickettsia. Accordingly, the subject invention concerns the discovery that DNA vaccines can induce protective immunity against rickettsial disease or death resulting therefrom.

BRIEF DESCRIPTION OF THE DRAWINGS

FIGS. 1A–1C show a comparison of the amino acid sequences from alignment of the three rickettsial proteins, namely, *Cowdria ruminantium* (C.r.), *Ehrlichia chaffeensis* (E.c.), and *Anaplasma marginale* (A.m.).

FIGS. 2A–2C shows the DNA sequence of the 28 kDa gene locus cloned from *E. chaffeensis* (FIGS. 2A–2B) and *E. canis* (FIG. 2C). One letter amino acid codes for the deduced protein sequences are presented below the nucleotide sequence. The proposed sigma-70-like promoter sequences (38) are presented in bold and underlined text as −10 and −35 (consensus −35 and −10 sequences are TTGACA and TATAAT, respectively). Similarly, consensus ribosomal binding sites and transcription terminator sequences (bold letter sequence) are identified. G-rich regions identified in the *E. chaffeensis* sequence are underlined. The conserved sequences from within the coding regions selected for RT-PCR assay are identified with italics and underlined text.

FIG. 3A shows the complete sequence of the MAP2 homolog of *Ehrlichia canis*. The arrow (→) represents the predicted start of the mature protein. The asterisk (*) represents the stop codon. Underlined nucleotides 5' to the open reading frame with −35 and −10 below represent predicted promoter sequences. Double underlined nucleotides represent the predicted ribosomal binding site. Underlined nucleotides 3' to the open reading frame represent possible transcription termination sequences.

FIG. 3B shows the complete sequence of the MAP2 homolog of *Ehrlichia chaffeensis*. The arrow (→) represents the predicted start of the mature protein. The asterisk (*) represents the stop codon. Underlined nucleotides 5' to the open reading frame with −35 and −10 below represent predicted promoter sequences. Double underlined nucleotides represent the predicted ribosomal binding site. Underlined nucleotides 3' to the open reading frame represent possible transcription termination sequences.

BRIEF DESCRIPTION OF THE SEQUENCES

SEQ ID NO. 1 is the coding sequence of the MAP1 gene from *Cowdria ruminantium* (Highway isolate).

SEQ ID NO. 2 is the polypeptide encoded by the polynucleotide of SEQ ID NO. 1.

SEQ ID NO. 3 is the coding sequence of the MAP1 gene from *Ehrlichia chaffeensis*.

SEQ ID NO. 4 is the polypeptide encoded by the polynucleotide of SEQ ID NO. 3.

SEQ ID NO. 5 is the *Anaplasma marginale* MSP4 gene coding sequence.

SEQ ID NO. 6 is the polypeptide encoded by the polynucleotide of SEQ ID NO. 5.

SEQ ID NO. 7 is a partial coding sequence of the VSA1 gene from *Ehrlichia chaffeensis*, also shown in FIGS. 2A–2B.

SEQ ID NO. 8 is the coding sequence of the VSA2 gene from *Ehrlichia chaffeensis*, also shown in FIGS. 2A–2B.

SEQ ID NO. 9 is the coding sequence of the VSA3 gene from *Ehrlichia chaffeensis*, also shown in FIGS. 2A–2B.

SEQ ID NO. 10 is the coding sequence of the VSA4 gene from *Ehrlichia chaffeensis*, also shown in FIGS. 2A–2B.

SEQ ID NO. 11 is a partial coding sequence of the VSA5 gene from *Ehrlichia chaffeensis*, also shown in FIGS. 2A–2B.

SEQ ID NO. 12 is the coding sequence of the VSA1 gene from *Ehrlichia canis*, also shown in FIG. 2C.

SEQ ID NO. 13 is a partial coding sequence of the VSA2 gene from *Ehrlichia canis*, also shown in FIG. 2C.

SEQ ID NO. 14 is the polypeptide encoded by the polynucleotide of SEQ ID NO. 7, also shown in FIGS. 2A–2B.

SEQ ID NO. 15 is the polypeptide encoded by the polynucleotide of SEQ ID NO. 8, also shown in FIGS. 2A–2B.

SEQ ID NO. 16 is the polypeptide encoded by the polynucleotide of SEQ ID NO. 9, also shown in FIGS. 2A–2B.

SEQ ID NO. 17 is the polypeptide encoded by the polynuceotide of SEQ ID NO. 10, also shown in FIGS. 2A–2B.

SEQ ID NO. 18 is the polypeptide encoded by the polynucleotide of SEQ ID NO. 11, also shown in FIGS. 2A–2B.

SEQ ID NO. 19 is the polypeptide encoded by the polynucleotide of SEQ ID NO. 12, also shown in FIG. 2C.

SEQ ID NO. 20 is the polypeptide encoded by the polynucleotide of SEQ ID NO. 13, also shown in FIG. 2C.

SEQ ID NO. 21 is the coding sequence of the MAP2 gene from *Ehrlichia canis*, also shown in FIG. 3A.

SEQ ID NO. 22 is the coding sequence of the MAP2 gene from *Ehrlichia chaffeensis*, also shown in FIG. 3B.

SEQ ID NO. 23 is the polypeptide encoded by the polynucleotide of SEQ ID NO. 21, also shown in FIG. 3A.

SEQ ID NO. 24 is the polypeptide encoded by the polynucleotide of SEQ ID NO. 22, also shown in FIG. 3B.

DETAILED DISCLOSURE OF THE INVENTION

In one embodiment, the subject invention concerns a novel strategy, termed nucleic acid vaccination, for eliciting an immune response protective against rickettsial disease. The subject invention also concerns novel compositions that can be employed according to this novel strategy for eliciting a protective immune response. According to the subject invention, recombinant plasmid DNA or mRNA encoding an antigen of interest is inoculated directly into the human or animal host where the antigen is expressed and an immune response induced. Advantageously, problems of protein purification, as can be encountered with antigen delivery using live vectors, can be virtually eliminated by employing the compositions or methods according to the subject invention. Unlike live vector delivery, the subject invention can provide a further advantage in that the DNA or RNA does not replicate in the host, but remains episomal with gene expression directed for as long as 19 months or more post-injection. See, for example, Wolff, J. A., J. J. Ludike, G. Acsadi, P. Williams, A. Jani (1992) *Hum. Mol. Genet.* 1:363. A complete immune response can be obtained as recombinant antigen is synthesized intracellularly and presented to the host immune system in the context of autologous class I and class II MHC molecules.

In one embodiment, the subject invention concerns nucleic acids and compositions comprising those nucleic acids that can be effective in protecting an animal from disease or death caused by rickettsia. For example, a nucleic acid vaccine of the subject invention has been shown to be protective against *Cowdria ruminantium*, the causative agent of heartwater in domestic ruminants. Accordingly, DNA sequences of rickettsial genes, e.g, MAP1 or homologues thereof, can be used as nucleic acid vaccines against human and animal rickettsial diseases. The MAP1 gene used to obtain this protection is also present in other rickettsiae including *Anaplasma marginale*, *Ehrlichia canis*, and in a causative agent of human ehrlichiosis, *Ehrlichia chaffeensis* (van Vliet, A., F. Jongejan, M. van Kleef, B. van der Zeijst [1994] *Infect. Immun.* 62:1451). The MAP1 gene or a MAP1-like gene can also be found in certain Rickettsia spp. MAP1-like genes from *Ehrlichia chaffeensis* and *Ehrlichia canis* have now been cloned and sequenced. These MAP-1 homologs are also referred to herein as Variable Surface Antigen (VSA) genes.

The present invention also concerns polynucleotides encoding MAP2 or MAP2 homologs from *Ehrlichia canis* and *Ehrlichia chaffeensis*. MAP2 polynucleotide sequences of the invention can be used as vaccine compositions and in diagnostic assays. The polynucleotides can also be used to produce the MAP2 polypeptides encoded thereby.

Compositions comprising the subject polynucleotides can include appropriate nucleic acid vaccine vectors (plasmids), which are commercially available (e.g., Vical, San Diego, Calif.). In addition, the compositions can include a pharmaceutically acceptable carrier, e.g., saline. The pharmaceutically acceptable carriers are well known in the art and also are commercially available. For example, such acceptable carriers are described in E. W. Martin's *Remington's Pharmaceutical Science*, Mack Publishing Company, Easton, Pa.

The subject invention also concerns polypeptides encoded by the subject polynucleotides. Specifically exemplified are the polypeptides encoded by the MAP-1 and VSA genes of *C. rumimontium*, *E. chaffeensis*, *E. canis* and the MP4 gene of *Anaplasma marginale*. Polypeptides encoded by *E. chaffeensis* and *E. canis* MAP2 genes are also exemplified herein.

Also encompassed within the scope of the present invention are fragments and variants of the exemplified polynucleotides. Variants include polynucleotides and/or polypeptides having base or amino acid additions, deletions and substitutions in the sequence of the subject molecule so long as those variants have substantially the same activity or serologic reactivity as the native molecules. Also included are allelic variants of the subject polynucleotides. The polypeptides and peptides of the present invention can be used to raise antibodies that are reactive with the polypeptides disclosed herein. The polypeptides and peptides can also be used as molecular weight markers.

Another aspect oft he subject invention concerns antibodies reactive with MAP-1 and MAP2 polypeptides disclosed herein. Antibodies can be monoclonal or polyclonal and can be produced using standard techniques known in the art. Antibodies of the invention can be used in diagnostic and therapeutic applications.

In a specific embodiment, the subject invention concerns a DNA vaccine (e.g., VCL1010/MAP1) containing the major antigenic protein 1 gene (MAP1) driven by the human cytomegalovirus (HCMV) enhancer-promoter injected intramuscularly into 8–10 week-old female DBA/2 mice after treating them with 50 $\mu$l/muscle of 0.5% bupivacaine 3 days previously. Up to 75% of the VCL1010/MAP1-immunized mice seroconverted and reacted with MAP1 in antigen blots. Splenocytes from immunized mice, but not from control mice immunized with VCLO1010 DNA (plasmid vector, Vical, San Diego) proliferated in response to recombinant MAP1 and *C. ruminantium* antigens in in vitro lymphocyte proliferation tests. These proliferating cells from mice immunized with VCL1010/MAP1 DNA secreted IFN-gamma and IL-2 at concentrations ranging from 610 pg/ml and 152 pg/ml to 1290 pg/ml and 310 pg/ml, respectively. In experiments testing different VCL1010/MAP1 DNA vaccine dose regimens (25–100 $\mu$g/dose, 2 or 4 immunizations), survival rates of 23% to 88% (35/92 survivors/total in all VCL1010/MAP1 immunized groups) were observed on challenge with 30LD50 of *C. ruminantium*. Survival rates of 0% to 3% (1/144 survivors/total in all control groups) were recorded for control mice immunized similarly with VCL1010 DNA or saline. Accordingly, the subject invention concerns the discovery that the gene encoding the MAP1 protein can induce protective immunity as a DNA vaccine against rickettsial disease.

The nucleic acid sequences described herein have other uses as well. For example, the nucleic acids of the subject invention can be useful as probes to identify complementary sequences within other nucleic acid molecules or genomes. Such use of probes can be applied to identify or distinguish infectious strains of organisms in diagnostic procedures or in rickettsial research where identification of particular organisms or strains is needed. As is well known in the art, probes can be made by labeling the nucleic acid sequences of interest according to accepted nucleic acid labeling procedures and techniques. A person of ordinary skill in the art would recognize that variations or fragments of the disclosed sequences which can specifically and selectively hybridize to the DNA of rickettsia can also function as a probe. It is within the ordinary skill of persons in the art, and does not require undue experimentation in view of the description provided herein, to determine whether a segment of the claimed DNA sequences is a fragment or variant which has characteristics of the full sequence, e.g., whether it specifically and selectively hybridizes or can confer protection against rickettsial infection in accordance with the subject invention. In addition, with the benefit of the subject disclosure describing the specific sequences, it is within the ordinary skill of those persons in the art to label hybridizing sequences to produce a probe.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. (1982) *Molecular Cloning: A Laboratory Manual*, Cold Spring Harbor Laboratory, New York; Wei et al. (1983) *J. Biol. Chem.* 258:13006–13512.

In addition, the nucleic acid sequences of the subject invention can be used as molecular weight markers in nucleic acid analysis procedures.

Following are examples which illustrate procedures for practicing the invention. These examples should not be construed as limiting. All percentages are by weight and all solvent mixture proportions are by volume unless otherwise noted.

Example 1

A nucleic acid vaccine construct was tested in animals for its ability to protect against death caused by infection with the rickettsia *Cowdria ruminantium*. The vaccine construct tested was the MAP1 gene of *C. ruminantium* inserted into plasmid VCL1010 (Vical, San Diego) under control of the human cytomegalovirus promoter-enhancer and intron A. In this study, seven groups containing 10 mice each were injected twice at 2-week intervals with either 100, 75, 50, or 25 $\mu$g VCL1001/MAP1 DNA (V/M in Table 1 below), or 100, 50 $\mu$g VCL1010 DNA (V in Table 1) or saline (Sal.), respectively. Two weeks after the last injections, 8 mice/group were challenged with 30LD50 of C. ruminantium and clinical symptoms and survival monitored. The remaining 2 mice/group were not challenged and were used for lymphocyte proliferation tests and cytokine measurements. The results of the study are summarized in Table 1, below:

TABLE 1

|  | 100 $\mu$g V/M | 75 $\mu$g V/M | 50 $\mu$g V/M | 25 $\mu$g V/M | 100 $\mu$g V | 50 $\mu$g V | Sal. |
|---|---|---|---|---|---|---|---|
| Survived | 5 | 7 | 5 | 3 | 0 | 0 | 0 |
| Died | 3 | 1 | 3 | 5 | 8 | 8 | 8 |

The VCL1010/MAP1 nucleic acid vaccine increased survival on challenge in all groups, with a total of 20/30 mice surviving compared to 0/24 in the control groups.

This study was repeated with another 6 groups, each containing 33 mice (a total of 198 mice). Three groups received 75 $\mu$g VCL1010/MAP1 DNA or VCL1010 DNA or saline (4 injections in all cases). Two weeks after the last injection, 30 mice/group were challenged with 30LD50 of *C. ruminantium* and 3 mice/group were sacrificed for lymphocyte proliferation tests and cytokine measurements. The results of this study are summarized in Table 2, below:

TABLE 2

|  | V/M 2 inj. | V 2 inj. | Sal. 2 inj. | V/M 4 inj. | V 4 inj. | Sal. 4 inj. |
|---|---|---|---|---|---|---|
| Survived | 7 | 0 | 0 | 8 | 0 | 1 |
| Died* | 23 | 30 | 30 | 22 | 30 | 29 |

*In mice that died in both V/M groups, there was an increase in mean survival time of approximately 4 days compared to the controls (p < 0.05).

Again, as summarized in Table 2, the VCLlO1010/MAP1 DNA vaccine increased the numbers of mice surviving in both immunized groups, although there was no apparent benefit of 2 additional injections. In these two experiments, there were a cumulative total of 35/92 (38%) surviving mice in groups receiving the VCL1010/MAP1 DNA vaccine compared to 1/144 (0.7%) surviving mice in the control groups. In both immunization and challenge trials described above, splenocytes from VCL1010/MAP1 immunized mice, but not from control mice, specifically proliferated to recombinant MAP1 protein and to *C. ruminantium* in lymphocyte proliferation tests. These proliferating splenocytes secreted IL-2 and gamma-interferon at concentrations up to 310 and 1290 pg/ml respectively. These data show that protection against rickettsial infections can be achieved with a DNA vaccine. In addition, these experiments show MAP1-related proteins as vaccine targets.

Example 2

The MAP1 protein of *C. ruminantium* has significant similarity to MSP4 of *A. marginale*, and related molecules may also be presenting other rickettsial pathogens. To prove this, we used primers based on regions conserved between *C. ruminantium* and *A. marginale* in PCR to clone a MAP1-like gene from *E. chaffeensis*. The amino acid sequence derived from the cloned *E. chaffeensis* MAP1-like gene, and alignment with the corresponding genes of *C. ruminantium* and *A. marginale* is shown in FIG. 1. We have now identified the regions of MAP1-like genes which are highly conserved between Ehrlichia, Cowdria, and Anaplasma and which can allow cloning of the analogous genes from other rickettsiae.

Example 3

Cloning and sequence analysis of MAP1 homologue genes of *E. chaffeensis* and *E. canis*

Genes homologous to the major surface protein of *C. ruminantium* MAP1 were cloned from *E. chaffeensis* and *E. canis* by using PCR cloning strategies. The cloned segments represent a 4.6 kb genomic locus of *E. chaffeensis* and a 1.6 kb locus of *E. canis*. DNA sequence generated from these clones was assembled and is presented along with the deduced amino acid sequence in FIGS. 2A–2B (SEQ ID NOS. 7–11 and 14–18) and FIG. 2C (SEQ ID NOS. 12–13 and 19–20). Significant features of the DNA include five very similar but nonidentical open reading frames (ORFs) for *E. chaffeensis* and two very similar, nonidentical ORFs for the *E. canis* cloned locus. The ORFs for both Ehrlichia spp. are separated by noncoding sequences ranging from 264 to 310 base pairs. The noncoding sequences have a higher A+T content (71.6% for *E. chaffeensis* and 76.1% for *E. canis*) than do the coding sequences (63.5% for *E. chaffeensis* and 68.0% for *E. canis*). A G-rich region –200 bases upstream from the initiation codon, sigma-70-like promoter sequences, putative ribosome binding sites (RBS), termination codons, and palindromic sequences near the termination codons are found in each of the *E. chaffeensis* noncoding sequences. The *E. canis* noncoding sequence has the same feature except for the G-rich region (FIG. 2C; SEQ ID NOS. 12–13 and 19–20).

Sequence comparisons of the ORFs at the nucleotide and translated amino acid levels revealed a high degree of similarity between them. The similarity spanned the entire coding sequences, except in three regions where notable sequence variations were observed including some deletions/insertions (Variable Regions I, II and III). Despite the similarities, no two ORFs are identical. The cloned ORF 2, 3 and 4 of E. chaffeensis have complete coding sequences. The ORF1 is a partial gene having only 143 amino acids at the C-terminus whereas the ORF5 is nearly complete but lacks 5–7 amino acids and a termination codon. The cloned ORF2 of *E. canis* also is a partial gene lacking a part of the C-terminal sequence. The overall similarity between different ORFs at the amino acid level is 56.0% to 85.4% for *E. chaffeensis,* whereas for *E. canis* it is 53.3%. The similarity of *E. chaffeensis* ORFs to the MAP1 coding sequences reported for *C. ruminantium* isolates ranged from 55.5% to 66.7%, while for *E. canis* to *C. ruminantium* it is 48.5% to 54.2%. Due to their high degree of similarity to MAP1 surface antigen genes of *C. ruminantium* and since they are nonidentical to each other, the *E. chaffeensis* and *E. canis* ORFs are referred to herein as putative Variable Surface Antigen (VSA) genes. The apparent molecular masses of the predicted mature proteins of *E. chaffeensis* were 28.75 kDa for VSA2, 27.78 for VSA3, and 27.95 for VSA4, while *E. canis* VSA1 was slightly higher at 29.03 kDa. The first 25 amino acids in each VSA coding sequence were eliminated when calculating the protein size since they markedly resembled the signal sequence of *C. ruminantium* MAP1 and presumably would be absent from the mature protein. Predicted protein sizes for *E. chaffeensis* VSA1 and VSA5, and *E. canis* VSA2 were not calculated since the complete genes were not cloned.

It should be understood that the examples and embodiments described herein are for illustrative purposes only and that various modifications or changes in light thereof will be suggested to persons skilled in the art and are to be included within the spirit and purview of this application and the scope of the appended claims.

SEQUENCE LISTING

```
<160> NUMBER OF SEQ ID NOS: 24

<210> SEQ ID NO 1
<211> LENGTH: 864
<212> TYPE: DNA
<213> ORGANISM: Cowdria ruminantium
<220> FEATURE:
<221> NAME/KEY: CDS
<222> LOCATION: (1)..(861)

<400> SEQUENCE: 1 atg aat tgc aag aaa att ttt atc aca agt aca cta ata tca tta gtg      48
Met Asn Cys Lys Lys Ile Phe Ile Thr Ser Thr Leu Ile Ser Leu Val
 1               5                  10                  15 tca ttt tta cct ggt gtg tcc ttt tct gat gta ata cag gaa gac agc      96
Ser Phe Leu Pro Gly Val Ser Phe Ser Asp Val Ile Gln Glu Asp Ser
                20                  25                  30 aac cca gca ggc agt gtt tac att agc gca aaa tac atg cca act gca     144
Asn Pro Ala Gly Ser Val Tyr Ile Ser Ala Lys Tyr Met Pro Thr Ala
            35                  40                  45 tca cat ttt ggt aaa atg tca atc aaa gaa gat tca aaa aat act caa     192
Ser His Phe Gly Lys Met Ser Ile Lys Glu Asp Ser Lys Asn Thr Gln
        50                  55                  60 acg gta ttt ggt cta aaa aaa gat tgg gat ggc gtt aaa aca cca tca     240
Thr Val Phe Gly Leu Lys Lys Asp Trp Asp Gly Val Lys Thr Pro Ser
 65                  70                  75                  80 gat tct agc aat act aat tct aca att ttt act gaa aaa gac tat tct     288
Asp Ser Ser Asn Thr Asn Ser Thr Ile Phe Thr Glu Lys Asp Tyr Ser
                85                  90                  95 ttc aga tat gaa aac aat ccg ttt tta ggt ttc gct gga gca att ggg     336
Phe Arg Tyr Glu Asn Asn Pro Phe Leu Gly Phe Ala Gly Ala Ile Gly
               100                 105                 110 tac tca atg aat gga cca aga ata gag ttc gaa gta tcc tat gaa act     384
Tyr Ser Met Asn Gly Pro Arg Ile Glu Phe Glu Val Ser Tyr Glu Thr
           115                 120                 125 ttt gat gta aaa aac cta ggt ggc aac tat aaa aac aac gca cac atg     432
Phe Asp Val Lys Asn Leu Gly Gly Asn Tyr Lys Asn Asn Ala His Met
```

-continued

```
              130                 135                 140
tac tgt gct tta gat aca gca gca caa aat agc act aat ggc gca gga      480
Tyr Cys Ala Leu Asp Thr Ala Ala Gln Asn Ser Thr Asn Gly Ala Gly
145                 150                 155                 160 tta act aca tct gtt atg gta aaa aac gaa aat tta aca aat ata tca      528
Leu Thr Thr Ser Val Met Val Lys Asn Glu Asn Leu Thr Asn Ile Ser
                    165                 170                 175 tta atg tta aat gcg tgt tat gat atc atg ctt gat gga ata cca gtt      576
Leu Met Leu Asn Ala Cys Tyr Asp Ile Met Leu Asp Gly Ile Pro Val
                180                 185                 190 tct cca tat gta tgt gca ggt att ggc act gac tta gtg tca gta att      624
Ser Pro Tyr Val Cys Ala Gly Ile Gly Thr Asp Leu Val Ser Val Ile
            195                 200                 205 aat gct aca aat cct aaa tta tct tat caa gga aag cta ggc ata agt      672
Asn Ala Thr Asn Pro Lys Leu Ser Tyr Gln Gly Lys Leu Gly Ile Ser
210                 215                 220 tac tca atc aat tct gaa gct tct atc ttt atc ggt gga cat ttc cat      720
Tyr Ser Ile Asn Ser Glu Ala Ser Ile Phe Ile Gly Gly His Phe His
225                 230                 235                 240 aga gtt ata ggt aat gaa ttt aaa gat att gct acc tta aaa ata ttt      768
Arg Val Ile Gly Asn Glu Phe Lys Asp Ile Ala Thr Leu Lys Ile Phe
                    245                 250                 255 act tca aaa aca gga ata tct aat cct ggc ttt gca tca gca aca ctt      816
Thr Ser Lys Thr Gly Ile Ser Asn Pro Gly Phe Ala Ser Ala Thr Leu
                260                 265                 270 gat gtt tgt cac ttt ggt ata gaa att gga gga agg ttt gta ttt taa     864
Asp Val Cys His Phe Gly Ile Glu Ile Gly Gly Arg Phe Val Phe
            275                 280                 285
```

<210> SEQ ID NO 2
<211> LENGTH: 287
<212> TYPE: PRT
<213> ORGANISM: Cowdria ruminantium

<400> SEQUENCE: 2

```
Met Asn Cys Lys Lys Ile Phe Ile Thr Ser Thr Leu Ile Ser Leu Val
 1               5                  10                  15

Ser Phe Leu Pro Gly Val Ser Phe Ser Asp Val Ile Gln Glu Asp Ser
                20                  25                  30

Asn Pro Ala Gly Ser Val Tyr Ile Ser Ala Lys Tyr Met Pro Thr Ala
            35                  40                  45

Ser His Phe Gly Lys Met Ser Ile Lys Glu Asp Ser Lys Asn Thr Gln
        50                  55                  60

Thr Val Phe Gly Leu Lys Lys Asp Trp Asp Gly Val Lys Thr Pro Ser
65                  70                  75                  80

Asp Ser Ser Asn Thr Asn Ser Thr Ile Phe Thr Glu Lys Asp Tyr Ser
                85                  90                  95

Phe Arg Tyr Glu Asn Asn Pro Phe Leu Gly Phe Ala Gly Ala Ile Gly
            100                 105                 110

Tyr Ser Met Asn Gly Pro Arg Ile Glu Phe Glu Val Ser Tyr Glu Thr
        115                 120                 125

Phe Asp Val Lys Asn Leu Gly Gly Asn Tyr Lys Asn Ala His Met
130                 135                 140

Tyr Cys Ala Leu Asp Thr Ala Ala Gln Asn Ser Thr Asn Gly Ala Gly
145                 150                 155                 160

Leu Thr Thr Ser Val Met Val Lys Asn Glu Asn Leu Thr Asn Ile Ser
                165                 170                 175
```

```
Leu Met Leu Asn Ala Cys Tyr Asp Ile Met Leu Asp Gly Ile Pro Val
            180                 185                 190

Ser Pro Tyr Val Cys Ala Gly Ile Gly Thr Asp Leu Val Ser Val Ile
            195                 200                 205

Asn Ala Thr Asn Pro Lys Leu Ser Tyr Gln Gly Lys Leu Gly Ile Ser
        210                 215                 220

Tyr Ser Ile Asn Ser Glu Ala Ser Ile Phe Ile Gly Gly His Phe His
225                 230                 235                 240

Arg Val Ile Gly Asn Glu Phe Lys Asp Ile Ala Thr Leu Lys Ile Phe
                245                 250                 255

Thr Ser Lys Thr Gly Ile Ser Asn Pro Gly Phe Ala Ser Ala Thr Leu
            260                 265                 270

Asp Val Cys His Phe Gly Ile Glu Ile Gly Gly Arg Phe Val Phe
            275                 280                 285

<210> SEQ ID NO 3
<211> LENGTH: 842
<212> TYPE: DNA
<213> ORGANISM: Ehrlichia chaffeensis
<220> FEATURE:
<221> NAME/KEY: CDS
<222> LOCATION: (1)..(840)

<400> SEQUENCE: 3
```

|

```
gca ggt atc ggt act gat tta gta tcc atg ttt gaa gct aca aat cct      624
Ala Gly Ile Gly Thr Asp Leu Val Ser Met Phe Glu Ala Thr Asn Pro
        195                 200                 205 aaa att tct tac caa gga aag tta ggt tta agc tac tct ata agc cca      672
Lys Ile Ser Tyr Gln Gly Lys Leu Gly Leu Ser Tyr Ser Ile Ser Pro
210                 215                 220 gaa gct tct gtg ttt att ggt ggg cac ttt cat aag gta ata ggg aac      720
Glu Ala Ser Val Phe Ile Gly Gly His Phe His Lys Val Ile Gly Asn
225                 230                 235                 240 gaa ttt aga gat att cct act ata ata cct act gga tca aca ctt gca      768
Glu Phe Arg Asp Ile Pro Thr Ile Ile Pro Thr Gly Ser Thr Leu Ala
            245                 250                 255 gga aaa gga aac tac cct gca ata gta ata ctg gat gta tgc cac ttt      816
Gly Lys Gly Asn Tyr Pro Ala Ile Val Ile Leu Asp Val Cys His Phe
        260                 265                 270 gga ata gaa atg gga gga agg ttt aa                                   842
Gly Ile Glu Met Gly Gly Arg Phe
        275                 280

<210> SEQ ID NO 4
<211> LENGTH: 280
<212> TYPE: PRT
<213> ORGANISM: Ehrlichia chaffeensis

<400> SEQUENCE: 4

Met Asn Tyr Lys Lys Ser Phe Ile Thr Ala Ile Asp Ile Ile Asn Ile
1               5                   10                  15

Leu Leu Leu Pro Gly Val Ser Phe Ser Asp Pro Arg Gln Val Val Val
            20                  25                  30

Ile Asn Gly Asn Phe Tyr Ile Ser Gly Lys Tyr Asp Ala Lys Ala Ser
        35                  40                  45

His Phe Gly Val Phe Ser Ala Lys Glu Glu Arg Asn Thr Thr Val Gly
    50                  55                  60

Val Phe Gly Leu Lys Gln Asn Trp Asp Gly Ser Ala Ile Ser Asn

-continued

```
                        245                 250                 255
Gly Lys Gly Asn Tyr Pro Ala Ile Val Ile Leu Asp Val Cys His Phe
            260                 265                 270
Gly Ile Glu Met Gly Gly Arg Phe
        275                 280

<210> SEQ ID NO 5
<211> LENGTH: 849
<212> TYPE: DNA
<213> ORGANISM: Anaplasma marginale
<220> FEATURE:
<221> NAME/KEY: CDS
<222> LOCATION: (1)..(846)

<400> SEQUENCE: 5 atg aat tac aga gaa ttg ttt aca ggg ggc ctg tca gca gcc aca gtc     48
Met Asn Tyr Arg Glu Leu Phe Thr Gly Gly Leu Ser Ala Ala Thr Val
  1               5                  10                  15 tgc gcc tgc tcc cta ctt gtt agt ggg gcc gta gtg gca tct ccc atg     96
Cys Ala Cys Ser Leu Leu Val Ser Gly Ala Val Val Ala Ser Pro Met
             20                  25                  30 agt cac gaa gtg gct tct gaa ggg gga gta atg gga ggt agc ttt tac    144
Ser His Glu Val Ala Ser Glu Gly Gly Val Met Gly Gly Ser Phe Tyr
         35                  40                  45 gtg ggt gcg gcc tac agc cca gca ttt cct tct gtt acc tcg ttc gac    192
Val Gly Ala Ala Tyr Ser Pro Ala Phe Pro Ser Val Thr Ser Phe Asp
     50                  55                  60 atg cgt gag tca agc aaa gag acc tca tac gtt aga ggc tat gac aag    240
Met Arg Glu Ser Ser Lys Glu Thr Ser Tyr Val Arg Gly Tyr Asp Lys
 65                  70                  75                  80 agc att gca acg att gat gtg agt gtg cca gca aac ttt tcc aaa tct    288
Ser Ile Ala Thr Ile Asp Val Ser Val Pro Ala Asn Phe Ser Lys Ser
                 85                  90                  95 ggc tac act ttt gcc ttc tct aaa aac tta atc acg tct ttc gac ggc    336
Gly Tyr Thr Phe Ala Phe Ser Lys Asn Leu Ile Thr Ser Phe Asp Gly
            100                 105                 110 gct gtg gga tat tct ctg gga gga gcc aga gtg gaa ttg gaa gcg agc    384
Ala Val Gly Tyr Ser Leu Gly Gly Ala Arg Val Glu Leu Glu Ala Ser
        115                 120                 125 tac aga agg ttt gct act ttg gcg gac ggg cag tac gca aaa agt ggt    432
Tyr Arg Arg Phe Ala Thr Leu Ala Asp Gly Gln Tyr Ala Lys Ser Gly
    130                 135                 140 gcg gaa tct ctg gca gct att acc cgc gac gct aac att act gag acc    480
Ala Glu Ser Leu Ala Ala Ile Thr Arg Asp Ala Asn Ile Thr Glu Thr
145                 150                 155                 160 aat tac ttc gta gtc aaa att gat gaa atc aca aac acc tca gtc atg    528
Asn Tyr Phe Val Val Lys Ile Asp Glu Ile Thr Asn Thr Ser Val Met
                165                 170                 175 tta aat ggc tgc tat gac gtg ctg cac aca gat tta cct gtg tcc ccg    576
Leu Asn Gly Cys Tyr Asp Val Leu His Thr Asp Leu Pro Val Ser Pro
            180                 185                 190 tat gta tgt gcc ggg ata ggc gca agc ttt gtt gac atc tct aag caa    624
Tyr Val Cys Ala Gly Ile Gly Ala Ser Phe Val Asp Ile Ser Lys Gln
        195                 200                 205 gta acc aca aag ctg gcc tac agg ggc aag gtt ggg att agc tac cag    672
Val Thr Thr Lys Leu Ala Tyr Arg Gly Lys Val Gly Ile Ser Tyr Gln
    210                 215                 220 ttt act ccg gaa ata tcc ttg gtg gca ggt ggg ttc tac cac ggg cta    720
Phe Thr Pro Glu Ile Ser Leu Val Ala Gly Gly Phe Tyr His Gly Leu
225                 230                 235                 240
```

```
ttt gat gag tct tac aag gac att ccc gca cac aac agt gta aag ttc      768
Phe Asp Glu Ser Tyr Lys Asp Ile Pro Ala His Asn Ser Val Lys Phe
            245                 250                 255 tct gga gaa gca aaa gcc tca gtc aaa gcg cat att gct gac tac ggc      816
Ser Gly Glu Ala Lys Ala Ser Val Lys Ala His Ile Ala Asp Tyr Gly
        260                 265                 270 ttt aac ctt gga gca aga ttc ctg ttc agc taa                          849
Phe Asn Leu Gly Ala Arg Phe Leu Phe Ser
        275                 280
```

<210> SEQ ID NO 6
<211> LENGTH: 282
<212> TYPE: PRT
<213> ORGANISM: Anaplasma marginale

<400> SEQUENCE: 6

```
Met Asn Tyr Arg Glu Leu Phe Thr Gly Gly Leu Ser Ala Ala Thr Val
 1               5                  10                  15

Cys Ala Cys Ser Leu Leu Val Ser Gly Ala Val Val Ala Ser Pro Met
            20                  25                  30

Ser His Glu Val Ala Ser Glu Gly Gly Val Met Gly Gly Ser Phe Tyr
        35                  40                  45

Val Gly Ala Ala Tyr Ser Pro Ala Phe Pro Ser Val Thr Ser Phe Asp
    50                  55                  60

Met Arg Glu Ser Ser Lys Glu Thr Ser Tyr Val Arg Gly Tyr Asp Lys
 65                 70                  75                  80

Ser Ile Ala Thr Ile Asp Val Ser Val Pro Ala Asn Phe Ser Lys Ser
                85                  90                  95

Gly Tyr Thr Phe Ala Phe Ser Lys Asn Leu Ile Thr Ser Phe Asp Gly
            100                 105                 110

Ala Val Gly Tyr Ser Leu Gly Gly Ala Arg Val Glu Leu Glu Ala Ser
        115                 120                 125

Tyr Arg Arg Phe Ala Thr Leu Ala Asp Gly Gln Tyr Ala Lys Ser Gly
    130                 135                 140

Ala Glu Ser Leu Ala Ala Ile Thr Arg Asp Ala Asn Ile Thr Glu Thr
145                 150                 155                 160

Asn Tyr Phe Val Val Lys Ile Asp Glu Ile Thr Asn Thr Ser Val Met
                165                 170                 175

Leu Asn Gly Cys Tyr Asp Val Leu His Thr Asp Leu Pro Val Ser Pro
            180                 185                 190

Tyr Val Cys Ala Gly Ile Gly Ala Ser Phe Val Asp Ile Ser Lys Gln
        195                 200                 205

Val Thr Thr Lys Leu Ala Tyr Arg Gly Lys Val Gly Ile Ser Tyr Gln
    210                 215                 220

Phe Thr Pro Glu Ile Ser Leu Val Ala Gly Phe Tyr His Gly Leu
225                 230                 235                 240

Phe Asp Glu Ser Tyr Lys Asp Ile Pro Ala His Asn Ser Val Lys Phe
                245                 250                 255

Ser Gly Glu Ala Lys Ala Ser Val Lys Ala His Ile Ala Asp Tyr Gly
            260                 265                 270

Phe Asn Leu Gly Ala Arg Phe Leu Phe Ser
        275                 280
```

<210> SEQ ID NO 7
<211> LENGTH: 132
<212> TYPE: DNA
<213> ORGANISM: Ehrlichia chaffeensis -continued

<400> SEQUENCE: 7

```
ggaatgaatt cagggacatt tctactctta aagcgtttgc tacaccatca tctgcagcta     60
ctccagactt agcaacagta acactgagtg tgtgtcactt tggagtagaa cttggaggaa    120
gatttaactt ct                                                        132
```

<210> SEQ ID NO 8
<211> LENGTH: 861
<212> TYPE: DNA
<213> ORGANISM: Ehrlichia chaffeensis

<400> SEQUENCE: 8

```
atatgaactg cgaaaaattt tttataacaa ctgcattaac attactaatg tccttcttac     60
ctggaatatc actttctgat ccagtacagg atgacaacat tagtggtaat ttctacatca    120
gtggaaagta tatgccaagc gcttcgcatt ttggagtttt ttctgccaag gaagaaagaa    180
atacaacagt tggagtattt ggaatagagc aagattggga tagatgtgta atatctagaa    240
ccactttaag cgatatattc accgttccaa attattcatt taagtatgaa aataatctat    300
tttcaggatt tgcaggagct attggctact caatggatgg cccaagaata gagcttgaag    360
tatcttatga agcattcgat gttaaaaatc aaggtaacaa ttataagaac gaagcacata    420
gatattatgc tctgtcccat cttctcggca cagagacaca gatagatggt gcaggcagtg    480
cgtctgtctt tctaataaat gaaggactac ttgataaatc atttatgctg aacgcatgtt    540
atgatgtaat aagtgaaggc atacctttttt ctccttatat atgtgcaggt attggtattg    600
atttagtatc catgtttgaa gctataaatc ctaaaatttc ttatcaagga aaattaggct    660
taagttaccc tataagccca gaagcttctg tgtttattgg tggacatttt cataaggtga    720
taggaaacga atttagagat attcctacta tgatacctag tgaatcagcg cttgcaggaa    780
aaggaaacta ccctgcaata gtaacactgg acgtgttcta ctttggcata gaacttggag    840
gaaggtttaa cttccaactt t                                              861
```

<210> SEQ ID NO 9
<211> LENGTH: 837
<212> TYPE: DNA
<213> ORGANISM: Ehrlichia chaffeensis

<400> SEQUENCE: 9

```
atatgaattg caaaaaattt tttataacaa ctgcattagt atcactaatg tcctttctac     60
ctggaatatc attttctgat ccagtgcaag gtgacaatat tagtggtaat ttctatgtta    120
gtggcaagta tatgccaagt gcttcgcatt ttggcatgtt ttctgccaaa gaagaaaaaa    180
atcctactgt tgcattgtat ggcttaaaac aagattggga agggattagc tcatcaagtc    240
acaatgataa tcatttcaat aacaagggtt attcatttaa atatgaaaat aacccatttt    300
tagggtttgc aggagctatt ggttattcaa tgggtggtcc aagagtagag tttgaagtgt    360
cctatgaaac atttgacgtt aaaaatcagg gtaataacta taaaaatgat gctcacagat    420
actgtgcttt aggtcaacaa gacaacagcg gaatacctaa aactagtaaa tacgtactgt    480
taaaaagcga aggattgctt gacatatcat ttatgctaaa tgcatgctat gatataataa    540
acgagagcat acctttgtct ccttacatat gtgcaggtgt tggtactgat ttaatatcca    600
tgtttgaagc tacaaatcct aaaatttctt accaagggaa gttaggtcta agttactcta    660
taaacccaga agcttctgta tttattggtg gacattttca taaggtgata ggaaacgaat    720
```

-continued

| | |
|---|---|
| ttagggacat tcctactctg aaagcatttg ttacgtcatc agctactcca gatctagcaa | 780 |
| tagtaacact aagtgtatgt cattttggaa tagaacttgg aggaaggttt aacttct | 837 |

<210> SEQ ID NO 10
<211> LENGTH: 843
<212> TYPE: DNA
<213> ORGANISM: Ehrlichia chaffeensis

<400> SEQUENCE: 10

| | |
|---|---|
| atatgaattg caaaaaattt tttataacaa ctacattagt atcgctaatg tccttcttac | 60 |
| ctggaatatc attttctgat gcagtacaga acgacaatgt tggtggtaat ttctatatca | 120 |
| gtgggaaata tgtaccaagt gtttcacatt ttggcgtatt ctctgctaaa caggaaagaa | 180 |
| atacaacaat cggagtattt ggattaaagc aagattggga tggcagcaca atatctaaaa | 240 |
| attctccaga aaatacattt aacgttccaa attattcatt taaatatgaa ataatccat | 300 |
| ttctaggttt tgcaggagct gttggttatt taatgaatgg tccaagaata gagttagaaa | 360 |
| tgtcctatga acatttgat gtgaaaaacc agggtaataa ctataagaac gatgctcaca | 420 |
| aatattatgc tttaacccat aacagtgggg gaaagctaag caatgcaggt gataagtttg | 480 |
| tttttctaaa aaatgaagga ctacttgata tatcacttat gttgaatgca tgctatgatg | 540 |
| taataagtga aggaatacct ttctctcctt acatatgtgc aggtgttggt actgatttaa | 600 |
| tatccatgtt tgaagctata aaccctaaaa tttcttatca aggaaagtta ggtttgagtt | 660 |
| actccataag cccagaagct tctgtttttg ttggtggaca ttttcataag gtgatagga | 720 |
| atgaattcag agatattcct gctatgatac ccagtacctc aactctcaca ggtaatcact | 780 |
| ttactatagt aacactaagt gtatgccact ttggagtgga acttggagga aggtttaact | 840 |
| ttt | 843 |

<210> SEQ ID NO 11
<211> LENGTH: 830
<212> TYPE: DNA
<213> ORGANISM: Ehrlichia chaffeensis

<400> SEQUENCE: 11

| | |
|---|---|
| atatgaatta caaaaaagtt ttcataacaa gtgcattgat atcattaata tcttctctac | 60 |
| ctggagtatc attttccgac ccagcaggta gtggtattaa cggtaatttc tacatcagtg | 120 |
| gaaaatacat gccaagtgct tcgcattttg gagtattctc tgctaaggaa gaaagaaata | 180 |
| caacagttgg agtgtttgga ctgaagcaaa attgggacgg aagcgcaata tccaactcct | 240 |
| ccccaaacga tgtattcact gtctcaaatt attcatttaa atatgaaaac aacccgtttt | 300 |
| taggttttgc aggagctatt ggttactcaa tggatggtcc aagaatagag cttgaagtat | 360 |
| cttatgaaac atttgatgta aaaaatcaag gtaacaatta taagaatgaa gcacatagat | 420 |
| attgtgctct atcccataac tcagcagcag acatgagtag tgcaagtaat aattttgtct | 480 |
| ttctaaaaaa tgaaggatta cttgacatat catttatgct gaacgcatgc tatgacgtag | 540 |
| taggcgaagg cataccttt tctccttata tatgcgcagg tatcggtact gatttagtat | 600 |
| ccatgtttga agctacaaat cctaaaattt cttaccaagg aaagttaggt ttaagctact | 660 |
| ctataagccc agaagcttct gtgtttattg gtgggcactt tcataaggta atagggaacg | 720 |
| aatttagaga tattcctact ataataccta ctggatcaac acttgcagga aaaggaaact | 780 |
| accctgcaat agtaatactg gatgtatgcc actttggaat agaaatggga | 830 |

<210> SEQ ID NO 12
<211> LENGTH: 864
<212> TYPE: DNA
<213> ORGANISM: Ehrlichia canis

<400> SEQUENCE: 12

```
atatgaaata taaaaaaact tttacagtaa ctgcattagt attattaact tcctttacac     60
attttatacc tttttatagt ccagcacgtg ccagtacaat tcacaacttc tacattagtg    120
gaaaatatat gccaacagcg tcacattttg gaatttttc agctaaagaa gaacaaagtt    180
ttactaaggt attagttggg ttagatcaac gattatcaca taatattata aacaataatg    240
atacagcaaa gagtcttaag gttcaaaatt attcatttaa atacaaaaat aacccatttc    300
taggatttgc aggagctatt ggttattcaa taggcaattc aagaatagaa ctagaagtat    360
cacatgaaat atttgatact aaaaacccag gaaacaatta tttaaatgac tctcacaaat    420
attgcgcttt atctcatgga agtcacatat gcagtgatgg aaatagcgga gattggtaca    480
ctgcaaaaac tgataagttt gtacttctga aaaatgaagg tttacttgac gtctcattta    540
tgttaaacgc atgttatgac ataacaactg aaaaaatgcc tttttcacct tatatatgtg    600
caggtattgg tactgatctc atatctatgt ttgagacaac acaaaacaaa atatcttatc    660
aaggaaagtt aggtttaaac tatactataa actcaagagt ttctgttttt gcaggtgggc    720
actttcataa ggtaataggt aatgaattta aaggtattcc tactctatta cctgatggat    780
caaacattaa agtacaacag tctgcaacag taacattaga tgtgtgccat ttcgggttag    840
agattggaag tagatttttc tttt                                           864
```

<210> SEQ ID NO 13
<211> LENGTH: 399
<212> TYPE: DNA
<213> ORGANISM: Ehrlichia canis

<400> SEQUENCE: 13

```
atatgaattg taaaaaagtt ttcacaataa gtgcattgat atcatccata tacttcctac     60
ctaatgtctc atactctaac ccagtatatg gtaacagtat gtatggtaat tttacatat    120 caggaaagta catgccaagt gttcctcatt ttggaatttt ttcagctgaa gaagagaaaa    180
aaaagacaac tgtagtatat ggcttaaaag aaaactgggc aggagatgca atatctagtc    240
aaagtccaga tgataatttt accattcgaa attactcatt caagtatgca agcaacaagt    300
ttttagggtt tgcagtagct attggttact cgataggcag tccaagaata gaagttgaga    360
tgtcttatga agcatttgat gtaaaaaatc aaggtaaca                           399
```

<210> SEQ ID NO 14
<211> LENGTH: 43
<212> TYPE: PRT
<213> ORGANISM: Ehrlichia chaffeensis

<400> SEQUENCE: 14

```
Asn Glu Phe Arg Asp Ile Ser Thr Leu Lys Ala Phe Ala Thr Pro Ser
  1               5                  10                  15

Ser Ala Ala Thr Pro Asp Leu Ala Thr Val Thr Leu Ser Val Cys His
             20                  25                  30

Phe Gly Val Glu Leu Gly Gly Arg Phe Asn Phe
         35                  40
```

<210> SEQ ID NO 15
<211> LENGTH: 286

-continued

```
<212> TYPE: PRT
<213> ORGANISM: Ehrlichia chaffeensis

<400> SEQUENCE: 15

Met Asn Cys Glu Lys Phe Phe Ile Thr Thr Ala Leu Thr Leu Leu Met
1 5 10 15

Ser Phe Leu Pro Gly Ile Ser Leu Ser Asp Pro Val Gln Asp Asp Asn
20 25 30

Ile Ser Gly Asn Phe Tyr Ile Ser Gly Lys Tyr Met Pro Ser Ala Ser
35 40 45

His Phe Gly Val Phe Ser Ala Lys Glu Glu Arg Asn Thr Thr Val Gly
50 55 60

Val Phe Gly Ile Glu Gln Asp Trp Asp Arg Cys Val Ile Ser Arg Thr
65 70 75 80

Thr Leu Ser Asp Ile Phe Thr Val Pro Asn Tyr Ser Phe Lys Tyr Glu
85 90 95

Asn Asn Leu Phe Ser Gly Phe Ala Gly Ala Ile Gly Tyr Ser Met Asp
100 105 110

Gly Pro Arg Ile Glu Leu Glu Val Ser Tyr Glu Ala Phe Asp Val Lys
115 120 125

Asn Gln Gly Asn Asn Tyr Lys Asn Glu Ala His Arg Tyr Tyr Ala Leu
130 135 140

Ser His Leu Leu Gly Thr Glu Thr Gln Ile Asp Gly Ala Gly Ser Ala
145 150 155 160

Ser Val Phe Leu Ile Asn Glu Gly Leu Leu Asp Lys Ser Phe Met Leu
165 170 175

Asn Ala Cys Tyr Asp Val Ile Ser Glu Gly Ile Pro Phe Ser Pro Tyr
180 185 190

Ile Cys Ala Gly Ile Gly Ile Asp Leu Val Ser Met Phe Glu Ala Ile
195 200 205

Asn Pro Lys Ile Ser Tyr Gln Gly Lys Leu Gly Leu Ser Tyr Pro Ile
210 215 220

Ser Pro Glu Ala Ser Val Phe Ile Gly Gly His Phe His Lys Val Ile
225 230 235 240

Gly Asn Glu Phe Arg Asp Ile Pro Thr Met Ile Pro Ser Glu Ser Ala
245 250 255

Leu Ala Gly Lys Gly Asn Tyr Pro Ala Ile Val Thr Leu Asp Val Phe
260 265 270

Tyr Phe Gly Ile Glu Leu Gly Gly Arg Phe Asn Phe Gln Leu
275 280 285

<210> SEQ ID NO 16
<211> LENGTH: 278
<212> TYPE: PRT
<213> ORGANISM: Ehrlichia chaffeensis

<400> SEQUENCE: 16

Met Asn Cys Lys Lys Phe Phe Ile Thr Thr Ala Leu Val Ser Leu Met
1 5 10 15

Ser Phe Leu Pro Gly Ile Ser Phe Ser Asp Pro Val Gln Gly Asp Asn
20 25 30

Ile Ser Gly Asn Phe Tyr Val Ser Gly Lys Tyr Met Pro Ser Ala Ser
35 40 45

His Phe Gly Met Phe Ser Ala Lys Glu Glu Lys Asn Pro Thr Val Ala
50 55 60
```

```
Leu Tyr Gly Leu Lys Gln Asp Trp Glu Gly Ile Ser Ser Ser His
 65                  70                  75                  80

Asn Asp Asn His Phe Asn Asn Lys Gly Tyr Ser Phe Lys Tyr Glu Asn
                 85                  90                  95

Asn Pro Phe Leu Gly Phe Ala Gly Ala Ile Gly Tyr Ser Met Gly Gly
            100                 105                 110

Pro Arg Val Glu Phe Glu Val Ser Tyr Glu Thr Phe Asp Val Lys Asn
            115                 120                 125

Gln Gly Asn Asn Tyr Lys Asn Asp Ala His Arg Tyr Cys Ala Leu Gly
        130                 135                 140

Gln Gln Asp Asn Ser Gly Ile Pro Lys Thr Ser Lys Tyr Val Leu Leu
145                 150                 155                 160

Lys Ser Glu Gly Leu Leu Asp Ile Ser Phe Met Leu Asn Ala Cys Tyr
                165                 170                 175

Asp Ile Ile Asn Glu Ser Ile Pro Leu Ser Pro Tyr Ile Cys Ala Gly
            180                 185                 190

Val Gly Thr Asp Leu Ile Ser Met Phe Glu Ala Thr Asn Pro Lys Ile
            195                 200                 205

Ser Tyr Gln Gly Lys Leu Gly Leu Ser Tyr Ser Ile Asn Pro Glu Ala
        210                 215                 220

Ser Val Phe Ile Gly Gly His Phe His Lys Val Ile Gly Asn Glu Phe
225                 230                 235                 240

Arg Asp Ile Pro Thr Leu Lys Ala Phe Val Thr Ser Ser Ala Thr Pro
                245                 250                 255

Asp Leu Ala Ile Val Thr Leu Ser Val Cys His Phe Gly Ile Glu Leu
            260                 265                 270

Gly Gly Arg Phe Asn Phe
            275

<210> SEQ ID NO 17
<211> LENGTH: 280
<212> TYPE: PRT
<213> ORGANISM: Ehrlichia chaffeensis

<400> SEQUENCE: 17

Met Asn Cys Lys Lys Phe Phe Ile Thr Thr Thr Leu Val Ser Leu Met
  1               5                  10                  15

Ser Phe Leu Pro Gly Ile Ser Phe Ser Asp Ala Val Gln Asn Asp Asn
                 20                  25                  30

Val Gly Gly Asn Phe Tyr Ile Ser Gly Lys Tyr Val Pro Ser Val Ser
             35                  40                  45

His Phe Gly Val Phe Ser Ala Lys Gln Glu Arg Asn Thr Thr Ile Gly
 50                  55                  60

Val Phe Gly Leu Lys Gln Asp Trp Asp Gly Ser Thr Ile Ser Lys Asn
 65                  70                  75                  80

Ser Pro Glu Asn Thr Phe Asn Val Pro Asn Tyr Ser Phe Lys Tyr Glu
                 85                  90                  95

Asn Asn Pro Phe Leu Gly Phe Ala Gly Ala Val Gly Tyr Leu Met Asn
            100                 105                 110

Gly Pro Arg Ile Glu Leu Glu Met Ser Tyr Glu Thr Phe Asp Val Lys
            115                 120                 125

Asn Gln Gly Asn Asn Tyr Lys Asn Asp Ala His Lys Tyr Tyr Ala Leu
        130                 135                 140

Thr His Asn Ser Gly Gly Lys Leu Ser Asn Ala Gly Asp Lys Phe Val
145                 150                 155                 160
```

-continued

```
Phe Leu Lys Asn Glu Gly Leu Leu Asp Ile Ser Leu Met Leu Asn Ala
                165                 170                 175
Cys Tyr Asp Val Ile Ser Glu Gly Ile Pro Phe Ser Pro Tyr Ile Cys
            180                 185                 190
Ala Gly Val Gly Thr Asp Leu Ile Ser Met Phe Glu Ala Ile Asn Pro
        195                 200                 205
Lys Ile Ser Tyr Gln Gly Lys Leu Gly Leu Ser Tyr Ser Ile Ser Pro
    210                 215                 220

Glu Ala Ser Val Phe Val Gly Gly His Phe His Lys Val Ile Gly Asn
225                 230                 235                 240
Glu Phe Arg Asp Ile Pro Ala Met Ile Pro Ser Thr Ser Thr Leu Thr
                245                 250                 255
Gly Asn His Phe Thr Ile Val Thr Leu Ser Val Cys His Phe Gly Val
            260                 265                 270

Glu Leu Gly Gly Arg Phe Asn Phe
        275                 280

<210> SEQ ID NO 18
<211> LENGTH: 276
<212> TYPE: PRT
<213> ORGANISM: Ehrlichia chaffeensis

<400> SEQUENCE: 18

Met Asn Tyr Lys Lys Val Phe Ile Thr Ser Ala Leu Ile Ser Leu Ile
  1               5                  10                  15

Ser Ser Leu Pro Gly Val Ser Phe Ser Asp Pro Ala Gly Ser Gly Ile
            20                  25                  30

Asn Gly Asn Phe Tyr Ile Ser Gly Lys Tyr Met Pro Ser Ala Ser His
        35                  40                  45

Phe Gly Val Phe Ser Ala Lys Glu Glu Arg Asn Thr Thr Val Gly Val
    50                  55                  60

Phe Gly Leu Lys Gln Asn Trp Asp Gly Ser Ala Ile Ser Asn Ser Ser
 65                  70                  75                  80

Pro Asn Asp Val Phe Thr Val Ser Asn Tyr Ser Phe Lys Tyr Glu Asn
                85                  90                  95

Asn Pro Phe Leu Gly Phe Ala Gly Ala Ile Gly Tyr Ser Met Asp Gly
            100                 105                 110

Pro Arg Ile Glu Leu Glu Val Ser Tyr Glu Thr Phe Asp Val Lys Asn
        115                 120                 125

Gln Gly Asn Asn Tyr Lys Asn Glu Ala His Arg Tyr Cys Ala Leu Ser
    130                 135                 140

His Asn Ser Ala Ala Asp Met Ser Ser Ala Ser Asn Asn Phe Val Phe
145                 150                 155                 160

Leu Lys Asn Glu Gly Leu Leu Asp Ile Ser Phe Met Leu Asn Ala Cys
                165                 170                 175

Tyr Asp Val Val Gly Glu Gly Ile Pro Phe Ser Pro Tyr Ile Cys Ala
            180                 185                 190

Gly Ile Gly Thr Asp Leu Val Ser Met Phe Glu Ala Thr Asn Pro Lys
        195                 200                 205

Ile Ser Tyr Gln Gly Lys Leu Gly Leu Ser Tyr Ser Ile Ser Pro Glu
    210                 215                 220

Ala Ser Val Phe Ile Gly Gly His Phe His Lys Val Ile Gly Asn Glu
225                 230                 235                 240

Phe Arg Asp Ile Pro Thr Ile Ile Pro Thr Gly Ser Thr Leu Ala Gly
```

-continued

```
                        245                 250                 255

Lys Gly Asn Tyr Pro Ala Ile Val Ile Leu Asp Val Cys His Phe Gly
                260                 265                 270

Ile Glu Met Gly
        275

<210> SEQ ID NO 19
<211> LENGTH: 287
<212> TYPE: PRT
<213> ORGANISM: Ehrlichia canis

<400> SEQUENCE: 19

Met Lys Tyr Lys Lys Thr Phe Thr Val Thr Ala Leu Val Leu Leu Thr
  1               5                  10                  15

Ser Phe Thr His Phe Ile Pro Phe Tyr Ser Pro Ala Arg Ala Ser Thr
                 20                  25                  30

Ile His Asn Phe Tyr Ile Ser Gly Lys Tyr Met Pro Thr Ala Ser His
             35                  40                  45

Phe Gly Ile Phe Ser Ala Lys Glu Gln Ser Phe Thr Lys Val Leu
         50                  55                  60

Val Gly Leu Asp Gln Arg Leu Ser His Asn Ile Ile Asn Asn Asn Asp
 65                  70                  75                  80

Thr Ala Lys Ser Leu Lys Val Gln Asn Tyr Ser Phe Lys Tyr Lys Asn
                 85                  90                  95

Asn Pro Phe Leu Gly Phe Ala Gly Ala Ile Gly Tyr Ser Ile Gly Asn
            100                 105                 110

Ser Arg Ile Glu Leu Glu Val Ser His Glu Ile Phe Asp Thr Lys Asn
        115                 120                 125

Pro Gly Asn Asn Tyr Leu Asn Asp Ser His Lys Tyr Cys Ala Leu Ser
    130                 135                 140

His Gly Ser His Ile Cys Ser Asp Gly Asn Ser Gly Asp Trp Tyr Thr
145                 150                 155                 160

Ala Lys Thr Asp Lys Phe Val Leu Leu Lys Asn Glu Gly Leu Leu Asp
                165                 170                 175

Val Ser Phe Met Leu Asn Ala Cys Tyr Asp Ile Thr Thr Glu Lys Met
            180                 185                 190

Pro Phe Ser Pro Tyr Ile Cys Ala Gly Ile Gly Thr Asp Leu Ile Ser
        195                 200                 205

Met Phe Glu Thr Thr Gln Asn Lys Ile Ser Tyr Gln Gly Lys Leu Gly
    210                 215                 220

Leu Asn Tyr Thr Ile Asn Ser Arg Val Ser Val Phe Ala Gly Gly His
225                 230                 235                 240

Phe His Lys Val Ile Gly Asn Glu Phe Lys Gly Ile Pro Thr Leu Leu
                245                 250                 255

Pro Asp Gly Ser Asn Ile Lys Val Gln Gln Ser Ala Thr Val Thr Leu
            260                 265                 270

Asp Val Cys His Phe Gly Leu Glu Ile Gly Ser Arg Phe Phe Phe
        275                 280                 285

<210> SEQ ID NO 20
<211> LENGTH: 133
<212> TYPE: PRT
<213> ORGANISM: Ehrlichia canis

<400> SEQUENCE: 20

Met Asn Cys Lys Lys Val Phe Thr Ile Ser Ala Leu Ile Ser Ser Ile
```

|   |   |   |   |   |
|---|---|---|---|---|
| 1 | 5 | | 10 | 15 |

Tyr Phe Leu Pro Asn Val Ser Tyr Ser Asn Pro Val Tyr Gly Asn Ser
               20                        25                       30

Met Tyr Gly Asn Phe Tyr Ile Ser Gly Lys Tyr Met Pro Ser Val Pro
         35                      40                      45

His Phe Gly Ile Phe Ser Ala Glu Glu Lys Lys Lys Thr Thr Val
     50                   55                  60

Val Tyr Gly Leu Lys Glu Asn Trp Ala Gly Asp Ala Ile Ser Ser Gln
65                 70                   75                  80

Ser Pro Asp Asp Asn Phe Thr Ile Arg Asn Tyr Ser Phe Lys Tyr Ala
               85                   90                  95

Ser Asn Lys Phe Leu Gly Phe Ala Val Ala Ile Gly Tyr Ser Ile Gly
         100                   105                110

Ser Pro Arg Ile Glu Val Glu Met Ser Tyr Glu Ala Phe Asp Val Lys
         115                  120                125

Asn Gln Gly Asn Asn
     130

<210> SEQ ID NO 21
<211> LENGTH: 686
<212> TYPE: DNA
<213> ORGANISM: Ehrlichia canis

<400> SEQUENCE: 21

```
atgaaagcta tcaaattcat acttaatgtc tgcttactat ttgcagcaat attttttaggg    60
tattcctata ttacaaaaca aggcatattt caaacaaaac atcatgatac acctaatact   120
actataccaa atgaagacgg tattcaatct agctttagct taatcaatca agacggtaaa   180
acagtaacca gccaagattt cctagggaaa cacatgttag ttttgtttgg attctctgca   240
tgtaaaagca tttgccctgc agaattggga ttagtatctg aagcacttgc acaacttggt   300
aataatgcag acaaattaca gtaattttt attacaattg atccaaaaaa tgatactgta   360
gaaaaattaa agaatttca tgaacatttt gattcaagaa ttcaaatgtt aacaggaaat   420
actgaagaca ttaatcaat aattaaaaat tataaaatat atgttggaca agcagataaa   480
gatcatcaaa ttaccattc tgcaataatg taccttattg acaaaaaagg atcatatctt   540
tcacacttca ttccagattt aaaatcacaa gaaaatcaag tagataagtt actatcttta   600
gttaagcagt atctgtaaat aaattcatgg aatacgttgg atgagtaggt ttttttttagt   660
atttttagtg ctaataacat tggcat                                        686
```

<210> SEQ ID NO 22
<211> LENGTH: 618
<212> TYPE: DNA
<213> ORGANISM: Ehrlichia chaffeensis

<400> SEQUENCE: 22

```
atgaaagtta tcaaatttat acttaatatc tgtttattat ttgcagcaat ttttctagga    60
tattcctacg taacaaaaca aggcattttt caagtaagag atcataacac tcccaataca   120
aatatatcaa ataaagccag cattactact agtttttcgt tagtaaatca agatggaaat   180
acagtaaata gtcaagattt tttgggaaaa tacatgctag ttttatttgg attttcttca   240
tgtaaaagca tctgccctgc tgaattagga atagcatctg aagttctctc acagcttggt   300
aatgacacag acaagttaca gtaattttc attacaattg atccaacaaa tgatactgta   360
caaaattaa aaacatttca tgaacatttt gatcctagaa ttcaaatgct aacaggcagt   420
```

```
gcagaagata ttgaaaaaat aataaaaaat tacaaaatat atgttggaca agcagataaa      480
gataatcaaa ttgatcactc tgccataatg tacattatcg ataaaaaagg agaatacatt      540
tcacactttt ctccagattt aaaatcaaca gaaaatcaag tagataagtt actatctata      600
ataaaacaat atctctaa                                                    618
```

```
<210> SEQ ID NO 23
<211> LENGTH: 205
<212> TYPE: PRT
<213> ORGANISM: Ehrlichia canis

<400> SEQUENCE: 23

Met Lys Ala Ile Lys Phe Ile Leu Asn Val Cys Leu Leu Phe Ala Ala
  1               5                  10                  15

Ile Phe Leu Gly Tyr Ser Tyr Ile Thr Lys Gln Gly Ile Phe Gln Thr
                 20                  25                  30

Lys His His Asp Thr Pro Asn Thr Thr Ile Pro Asn Glu Asp Gly Ile
             35                  40                  45

Gln Ser Ser Phe Ser Leu Ile Asn Gln Asp Gly Lys Thr Val Thr Ser
 50                  55                  60

Gln Asp Phe Leu Gly Lys His Met Leu Val Leu Phe Gly Phe Ser Ala
 65                  70                  75                  80

Cys Lys Ser Ile Cys Pro Ala Glu Leu Gly Leu Val Ser Glu Ala Leu
                 85                  90                  95

Ala Gln Leu Gly Asn Asn Ala Asp Lys Leu Gln Val Ile Phe Ile Thr
                100                 105                 110

Ile Asp Pro Lys Asn Asp Thr Val Glu Lys Leu Lys Glu Phe His Glu
            115                 120                 125

His Phe Asp Ser Arg Ile Gln Met Leu Thr Gly Asn Thr Glu Asp Ile
130                 135                 140

Asn Gln Ile Ile Lys Asn Tyr Lys Ile Tyr Val Gly Gln Ala Asp Lys
145                 150                 155                 160

Asp His Gln Ile Asn His Ser Ala Ile Met Tyr Leu Ile Asp Lys Lys
                165                 170                 175

Gly Ser Tyr Leu Ser His Phe Ile Pro Asp Leu Lys Ser Gln Glu Asn
                180                 185                 190

Gln Val Asp Lys Leu Leu Ser Leu Val Lys Gln Tyr Leu
            195                 200                 205

<210> SEQ ID NO 24
<211> LENGTH: 205
<212> TYPE: PRT
<213> ORGANISM: Ehrlichia chaffeensis

<400> SEQUENCE: 24

Met Lys Val Ile Lys Phe Ile Leu Asn Ile Cys Leu Leu Phe Ala Ala
  1               5                  10                  15

Ile Phe Leu Gly Tyr Ser Tyr Val Thr Lys Gln Gly Ile Phe Gln Val
                 20                  25                  30

Arg Asp His Asn Thr Pro Asn Thr Asn Ile Ser Asn Lys Ala Ser Ile
             35                  40                  45

Thr Thr Ser Phe Ser Leu Val Asn Gln Asp Gly Asn Thr Val Asn Ser
 50                  55                  60

Gln Asp Phe Leu Gly Lys Tyr Met Leu Val Leu Phe Gly Phe Ser Ser
 65                  70                  75                  80
```

-continued

```
Cys Lys Ser Ile Cys Pro Ala Glu Leu Gly Ile Ala Ser Glu Val Leu
            85                  90                  95

Ser Gln Leu Gly Asn Asp Thr Asp Lys Leu Gln Val Ile Phe Ile Thr
            100                 105                 110

Ile Asp Pro Thr Asn Asp Thr Val Gln Lys Leu Lys Thr Phe His Glu
            115                 120                 125

His Phe Asp Pro Arg Ile Gln Met Leu Thr Gly Ser Ala Glu Asp Ile
            130                 135                 140

Glu Lys Ile Ile Lys Asn Tyr Lys Ile Tyr Val Gly Gln Ala Asp Lys
145                 150                 155                 160

Asp Asn Gln Ile Asp His Ser Ala Ile Met Tyr Ile Ile Asp Lys Lys
                165                 170                 175

Gly Glu Tyr Ile Ser His Phe Ser Pro Asp Leu Lys Ser Thr Glu Asn
            180                 185                 190

Gln Val Asp Lys Leu Leu Ser Ile Ile Lys Gln Tyr Leu
            195                 200                 205
```

What is claimed is:

1. A method of inducing an immune response to a rickettsial polypeptide comprising the amino acid sequence of SEQ ID NO:23 or SEQ ID NO: 24 in an animal comprising the administration of a composition comprising a pharmaceutically acceptable carrier and nucleic acid vaccine vector containing an operably linked isolated polynucleotide encoding a polypeptide comprising the amino acid sequence of SEQ ID NO: 23 or SEQ ID NO: 24, wherein said composition is administered in an amount effective to elicit an immune response.

2. The method, according to claim 1, wherein said polypeptide has the sequence shown in SEQ ID NO:23.

3. The method, according to claim 1, wherein said polypeptide has the sequence shown in SEQ ID NO:24.

4. The method, according to claim 1, wherein said nucleic acid further comprises a nucleic acid vector.

5. An isolated polynucleotide encoding a polypeptide comprising the amino acid sequence of SEQ ID NO: 23 or SEQ ID NO: 24.

6. A composition comprising an isolated polynucleotide encoding a polypeptide comprising the amino acid sequence of SEQ ID NO: 23 or SEQ ID NO: 24 and a pharmaceutically acceptable carrier.

7. A vector comprising an isolated polynucleotide encoding a polypeptide comprising the amino acid sequence of SEQ ID NO: 23 or SEQ ID NO: 24.

8. A composition comprising a vector containing an isolated polynucleotide encoding a polypeptide comprising the amino acid sequence of SEQ ID NO: 23 or SEQ ID NO: 24 and a pharmaceutically acceptable carrier.

9. The composition of claim 8, wherein said vector is a vaccine vector.

* * * * *

UNITED STATES PATENT AND TRADEMARK OFFICE
CERTIFICATE OF CORRECTION

PATENT NO. : 6,251,872 B1
DATED : June 26, 2001
INVENTOR(S) : Barbet et al.

It is certified that error appears in the above-identified patent and that said Letters Patent is hereby corrected as shown below:

<u>Title page,</u>
ABSTRACT,
Line 1, "nucleric" should read -- nucleic --.

<u>Column 2,</u>
Line 16, "*Med*" should read -- *Med.* --.

<u>Column 4,</u>
Line 12, "-10below" should read -- -10 below --.

<u>Column 6,</u>
Line 32, "oft he" should read -- of the --.

<u>Column 7,</u>
Line 49, "VCL1001/MAP1" should read -- VCL1010/MAP1 --.

<u>Column 8,</u>
Line 18, "VCL1O1010/MAP1" should read -- VCL1010/MAP1 --.

Signed and Sealed this

Sixteenth Day of April, 2002

*Attest:*

JAMES E. ROGAN
*Attesting Officer*     *Director of the United States Patent and Trademark Office*